United States Patent
Herron et al.

(10) Patent No.: US 10,804,473 B2
(45) Date of Patent: Oct. 13, 2020

(54) ELECTRON TRANSPORT MATERIALS FOR ELECTRONIC APPLICATIONS

(71) Applicant: LG Chem, Ltd., Seoul (KR)

(72) Inventors: Norman Herron, Newark, DE (US); Htay Min Hlaing, Wilmington, DE (US)

(73) Assignee: LG Chem, Ltd. (KR)

(*) Notice: Subject to any disclaimer, the term of this patent is extended or adjusted under 35 U.S.C. 154(b) by 592 days.

(21) Appl. No.: 15/147,579

(22) Filed: May 5, 2016

(65) Prior Publication Data

US 2016/0343957 A1    Nov. 24, 2016

Related U.S. Application Data

(60) Provisional application No. 62/164,647, filed on May 21, 2015.

(51) Int. Cl.
*H01L 51/00* (2006.01)
*C07D 471/04* (2006.01)
(Continued)

(52) U.S. Cl.
CPC ........ *H01L 51/0072* (2013.01); *C07D 471/04* (2013.01); *C09K 11/025* (2013.01);
(Continued)

(58) Field of Classification Search
CPC .................................................. H01L 51/0072
See application file for complete search history.

(56) References Cited

U.S. PATENT DOCUMENTS 6,670,645 B2   12/2003   Grushin et al.
6,875,524 B2   4/2005   Hatwar et al.
(Continued)

FOREIGN PATENT DOCUMENTS

KR    20140141337 A   * 12/2014
WO    2003/040257 A1    5/2003
(Continued)

OTHER PUBLICATIONS

English machine translation of Han et al. (KR 2014/0141337 A) provided by the EPO. (Year: 2018).*
(Continued)

*Primary Examiner* — Daniel P Malley, Jr.
(74) *Attorney, Agent, or Firm* — Lerner, David, Littenberg, Krumholz & Mentlik, LLP

(57) ABSTRACT

There is provided a compound having Formula I

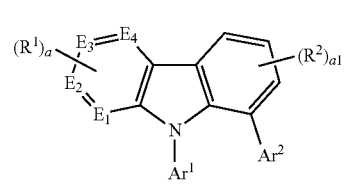

(I)

In Formula I: $E_1$-$E_4$ are CH, CD, or N, where one and only one of $E_1$-$E_4$ is N; $Ar^1$ is an N-heterocycle or a deuterated N-heterocycle; $Ar^2$ is aryl, heteroaryl, diarylamino, or deuterated analogs thereof; $R^1$ and $R^2$ are the same or different and are D, alkyl, silyl, aryl, heteroaryl, deuterated alkyl, deuterated silyl, deuterated aryl, or deuterated heteroaryl; and a and a1 are the same or different and are integers from 0-3.

11 Claims, 2 Drawing Sheets

(51) Int. Cl.
*C09K 11/02* (2006.01)
*C09K 11/06* (2006.01)
*H01L 51/50* (2006.01)

(52) U.S. Cl.
CPC .......... *C09K 11/06* (2013.01); *H01L 51/0059* (2013.01); *H01L 51/0067* (2013.01); *C09K 2211/1007* (2013.01); *C09K 2211/1029* (2013.01); *C09K 2211/185* (2013.01); *H01L 51/5016* (2013.01); *H01L 51/5024* (2013.01); *H01L 2251/5384* (2013.01)

(56) References Cited

U.S. PATENT DOCUMENTS

| | | | |
|---|---|---|---|
| 7,351,358 | B2 | 4/2008 | Hsu et al. |
| 2004/0102577 | A1 | 5/2004 | Hsu et al. |
| 2004/0127637 | A1 | 7/2004 | Hsu et al. |
| 2005/0158577 | A1 | 7/2005 | Ishibashi et al. |
| 2005/0205860 | A1 | 9/2005 | Hsu et al. |
| 2007/0063638 | A1 | 3/2007 | Tokairin et al. |
| 2007/0292713 | A9 | 12/2007 | Dobbs et al. |
| 2015/0001471 | A1* | 1/2015 | Boudreault ......... H01L 51/0067 257/40 |
| 2015/0349273 | A1* | 12/2015 | Hung ................. H01L 51/0072 257/40 |

FOREIGN PATENT DOCUMENTS

| | | | |
|---|---|---|---|
| WO | 2003/063555 | A1 | 7/2003 |
| WO | 2004/016710 | A1 | 2/2004 |
| WO | 2007/021117 | A1 | 2/2007 |
| WO | 2009/018009 | A1 | 2/2009 |
| WO | 2011/053334 | A1 | 5/2011 |
| WO | 2011/159872 | A1 | 12/2011 |
| WO | 2012/087955 | A1 | 6/2012 |
| WO | 2013/142634 | A1 | 9/2013 |
| WO | WO-2014021569 | A1 * | 2/2014 ............ H05B 33/14 |
| WO | 2015/089304 | A1 | 6/2015 |

OTHER PUBLICATIONS

Wang, Y., Kirk-Othmer Encyclopedia of Chemical Technology, Fourth Edition, 1996, vol. 18, pp. 837-860 (Book Not Included).

Gustafsson, G. et al. "Flexible light-emitting diodes made from soluble conducting polymers," Letters to Nature, Jun. 11, 1992, vol. 357, pp. 477-479.

Electronics and Nucleonics Dictionary, 1966, pp. 470 and 476, McGraw Hill, Inc.

CRC Handbook of Chemistry and Physics, 81st Edition, 2000-2001 (Book Not Included).

* cited by examiner

ELECTRON TRANSPORT MATERIALS FOR ELECTRONIC APPLICATIONS

CLAIM OF BENEFIT OF PRIOR APPLICATION

This application claims the benefit of U.S. Provisional Application No. 62/164,647, filed May 21, 2015, which is incorporated in its entirety herein by reference.

BACKGROUND INFORMATION

Field of the Disclosure

This disclosure relates in general to new electron transporting compounds. It also relates to organic electronic devices including at least one layer having the new compound.

Description of the Related Art

In organic photoactive electronic devices, such as organic light emitting diodes ("OLED"), that make up OLED displays, the organic electroactive layer is sandwiched between two electrical contact layers in an OLED display. In an OLED, the organic photoactive layer emits light through the light-transmitting electrical contact layer upon application of a voltage across the electrical contact layers.

It is well known to use organic electroluminescent compounds as the electroactive component in light-emitting diodes. Simple organic molecules, conjugated polymers, and organometallic complexes have been used.

Devices that use photoactive materials frequently include one or more charge transport layers, which are positioned between a photoactive (e.g., light-emitting) layer and a contact layer (hole-injecting contact layer). A device can contain two or more contact layers. A hole transport layer can be positioned between the photoactive layer and the hole-injecting contact layer. The hole-injecting contact layer may also be called the anode. An electron transport layer can be positioned between the photoactive layer and the electron-injecting contact layer. The electron-injecting contact layer may also be called the cathode. Charge transport materials can also be used as hosts in combination with the photoactive materials.

There is a continuing need for new materials for electronic devices.

SUMMARY

There is provided a compound having Formula I

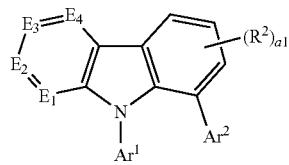

(I)

wherein:
E$_1$-E$_4$ are selected from the group consisting of CH, CD, CR$^1$, and N, where one and only one of E$_1$-E$_4$ is N;
Ar$^1$ is selected from the group consisting of an N-heterocycle and a deuterated N-heterocycle;
Ar$^2$ is selected from the group consisting of hydrocarbon aryl, heteroaryl, diarylamino, N-carbazolyl, substituted derivatives thereof, and deuterated analogs thereof;
R$^1$ and R$^2$ are the same or different at each occurrence and are selected from the group consisting of D, alkyl, silyl, germyl, hydrocarbon aryl, heteroaryl, deuterated alkyl, deuterated silyl, deuterated germyl, deuterated hydrocarbon aryl, and deuterated heteroaryl; and
a1 is an integer from 0-3.

There is also provided a compound having Formula II-A

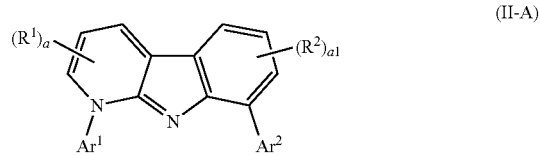

(II-A)

where a is an integer from 0-3, and Ar$^1$, Ar$^2$, R$^1$, R$^2$, and a1 are as defined above for Formula I.

There is also provided a compound having Formula II-B

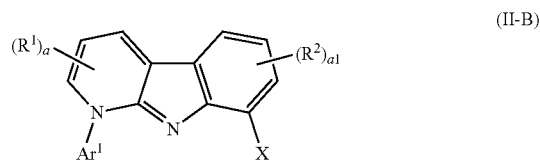

(II-B)

where X is halide and Ar$^1$, R$^1$, R$^2$, a and a1 are as defined above for Formula II-A.

There is also provided a compound having Formula II

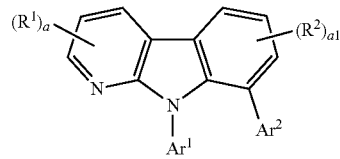

where Ar$^1$, Ar$^2$, R$^1$, R$^2$, a and a1 are as defined above for Formula I and Formula II-A.

There is also a compound having one of Formula III, Formula IV, and Formula V

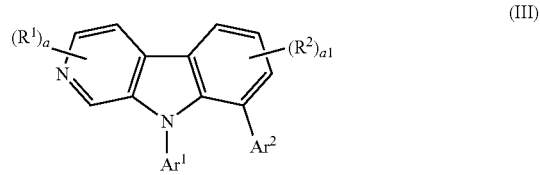

(III)

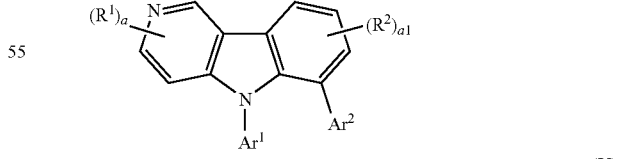

(IV)

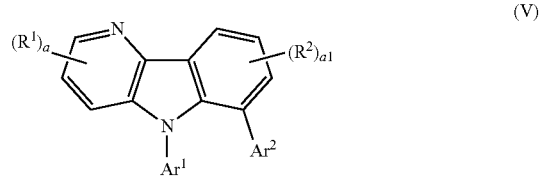

(V)

where Ar¹, Ar², R¹, R², a and a1 are as defined above for Formula II.

There is also provided a process of making a Z-azacarbazole derivative from a Z-aza-8-halo-carbazole compound in an inert atmosphere, where Z=1, 2, 3, or 4, comprising:
(1) treating the Z-aza-8-halo-carbazole compound with
  (a) an aryl-boronic acid derivative or aryl-boronate ester derivative in the presence of a zerovalent metal catalyst;
  or
  (b) a diarylamine or carbazole compound in the presence of a zerovalent metal catalyst and an anhydrous strong base;
  or
  (c) a halide derivative of an N-heterocycle in the presence of an anhydrous strong base;
(2a) if 1(a) or 1(b), treating the reaction product of step (1) with a halide derivative of an N-heterocycle in the presence of an anhydrous strong base, then heating to a temperature of 200° C. or greater;
  (2b) if 1(c), heating the reaction product of Step (1) to a temperature of 200° C. or greater, then treating the heated reaction product with either (i) an aryl-boronic acid derivative or aryl-boronate ester derivative in the presence of a zerovalent metal catalyst or
    (ii) a diarylamine or carbazole compound in the presence of anhydrous strong base;
whereby a Z-azacarbazole compound having a substituent at position 8 which is an aryl, diarylamino, or N-carbazolyl group and a substituent at position 9 which is an N-heterocycle is formed.

There is also provided a composition comprising (a) a host compound having Formula I, Formula II, Formula III, Formula IV, or
Formula V and (b) a dopant capable of electroluminescence having an emission maximum between 380 and 750 nm.

There is also provided an electronic device comprising at least one layer comprising the compound having Formula I, Formula II, Formula III, Formula IV, or Formula V.

There is also provided an electronic device comprising at least one electroactive layer positioned between two electrical contact layers, wherein the at least one electroactive layer of the device includes an electroactive compound having Formula I, Formula II, Formula III, Formula IV, or Formula V.

The foregoing general description and the following detailed description are exemplary and explanatory only and are not restrictive of the invention, as defined in the appended claims.

BRIEF DESCRIPTION OF THE DRAWINGS

Embodiments are illustrated in the accompanying figures to improve understanding of concepts as presented herein.

Figure 1:
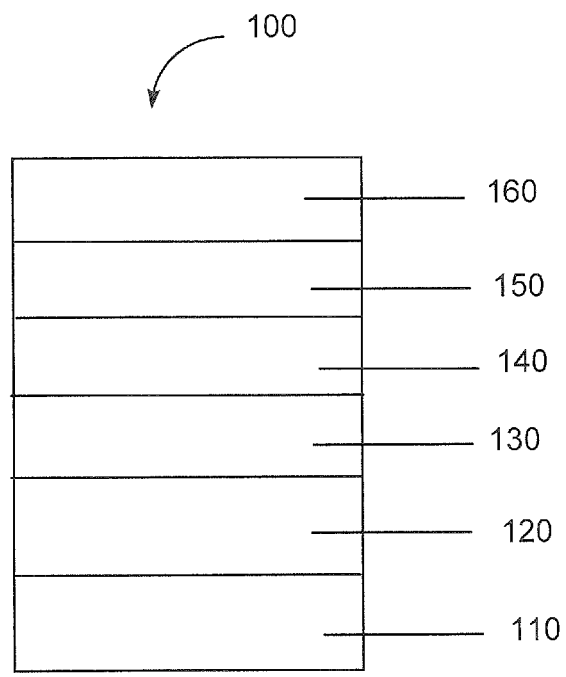
FIG. 1 includes an illustration of one example of an organic electronic device.

Skilled artisans appreciate that objects in the figures are illustrated for simplicity and clarity and have not necessarily been drawn to scale. For example, the dimensions of some of the objects in the figures may be exaggerated relative to other objects to help to improve understanding of embodiments.

DETAILED DESCRIPTION

Many aspects and embodiments have been described above and are merely exemplary and not limiting. After reading this specification, skilled artisans appreciate that other aspects and embodiments are possible without departing from the scope of the invention.

Other features and benefits of any one or more of the embodiments will be apparent from the following detailed description, and from the claims. The detailed description first addresses Definitions and Clarification of Terms followed by the Compounds of Formulae I-V, Synthesis, the Electroactive Composition, the Electronic Device, and finally Examples.

1. DEFINITIONS AND CLARIFICATION OF TERMS

Before addressing details of embodiments described below, some terms are defined or clarified.

As used in the "Definitions and Clarification of Terms", $R_3$, R' and R" and any other variables are generic designations and may be the same as or different from those defined in the formulas.

The term "alkyl" is intended to mean a group derived from an aliphatic hydrocarbon.

The term "aryl" is intended to mean a group derived from an aromatic hydrocarbon. The term "aromatic compound" is intended to mean an organic compound comprising at least one unsaturated cyclic group having 4n+2 delocalized pi electrons. The term is intended to encompass both aromatic compounds having only carbon and hydrogen atoms, and heteroaromatic compounds wherein one or more of the carbon atoms within the cyclic group has been replaced by another atom, such as nitrogen, oxygen, sulfur, or the like. The term "hydrocarbon aromatic compound" or "hydrocarbon aryl" refers to an aromatic compound or aryl group having only carbon atoms within the cyclic rings.

The term "carbazolyl" refers to a group containing the unit

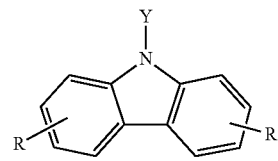

where R is H, D, alkyl, aryl, or a point of attachment and Y is aryl or a point of attachment. The term N-carbazolyl refers to a carbazolyl group where Y is the point of attachment.

The term "charge transport," when referring to a layer, material, member, or structure is intended to mean such layer, material, member, or structure facilitates migration of such charge through the thickness of such layer, material, member, or structure with relative efficiency and small loss of charge. Hole transport materials facilitate positive charge; electron transport material facilitate negative charge. Although photoactive materials may also have some charge transport properties, the term "charge transport layer, material, member, or structure" is not intended to include a layer, material, member, or structure whose primary function is light emission or light reception.

The term "deuterated" is intended to mean that at least one hydrogen ("H") has been replaced by deuterium ("D"). The term "deuterated analog" refers to a structural analog of a compound or group in which one or more available hydrogens have been replaced with deuterium. In a deuterated compound or deuterated analog, the deuterium is present in at least 100 times the natural abundance level. In some embodiments, the compound is at least 10% deuterated. The terms "% deuterated" or "% deuteration" mean the ratio of deuterons to the sum of protons plus deuterons, expressed as a percentage.

The term "dopant" is intended to mean a material, within a layer including a host material, that changes the electronic characteristic(s) or the targeted wavelength(s) of radiation emission, reception, or filtering of the layer compared to the electronic characteristic(s) or the wavelength(s) of radiation emission, reception, or filtering of the layer in the absence of such material.

The term "electroactive" when referring to a layer or material, is intended to mean a layer or material that exhibits electronic or electro-radiative properties. In an electronic device, an electroactive material electronically facilitates the operation of the device. Examples of electroactive materials include, but are not limited to, materials which conduct, inject, transport, or block a charge, where the charge can be either an electron or a hole, and materials which emit radiation or exhibit a change in concentration of electron-hole pairs when receiving radiation. Examples of inactive materials include, but are not limited to, planarization materials, insulating materials, and environmental barrier materials.

The term "germyl" refers to the group $R_3Ge$—, where R is the same or different at each occurrence and is H, D, C1-20 alkyl, deuterated alkyl, fluoroalkyl, aryl, or deuterated aryl. In some embodiments, R is selected from C1-20 alkyl, deuterated alkyl, fluoroalkyl, aryl, deuterated aryl, and combinations thereof.

The term "host material" is intended to mean a material, usually in the form of a layer, to which a dopant may or may not be added. The host material may or may not have electronic characteristic(s) or the ability to emit, receive, or filter radiation.

The term "hydrocarbon aryl" is intended to mean an aryl group containing only hydrogen and carbon atoms.

The term "layer" is used interchangeably with the term "film" and refers to a coating covering a desired area. The term is not limited by size. The area can be as large as an entire device or as small as a specific functional area such as the actual visual display, or as small as a single sub-pixel. Layers and films can be formed by any conventional deposition technique, including vapor deposition, liquid deposition (continuous and discontinuous techniques), and thermal transfer. Continuous deposition techniques, include but are not limited to, spin coating, gravure coating, curtain coating, dip coating, slot-die coating, spray coating, and continuous nozzle coating. Discontinuous deposition techniques include, but are not limited to, ink jet printing, gravure printing, and screen printing.

The term "N-heterocycle" refers to a heteroaromatic compound or group having at least one nitrogen in an aromatic ring.

The term "organic electronic device," or sometimes just "electronic device," is intended to mean a device including one or more organic semiconductor layers or materials.

The term "photoactive" is intended to mean a material or layer that emits light when activated by an applied voltage (such as in a light emitting diode or chemical cell) or responds to radiant energy and generates a signal with or without an applied bias voltage (such as in a photodetector).

The term "siloxane" refers to the group $R_3SiOR_2Si$—, where R is the same or different at each occurrence and is H, D, C1-20 alkyl, deuterated alkyl, fluoroalkyl, aryl, or deuterated aryl. In some embodiments, one or more carbons in an R alkyl group are replaced with Si.

The term "siloxy" refers to to the group $R_3SiO$—, where R is the same or different at each occurrence and is H, D, C1-20 alkyl, deuterated alkyl, fluoroalkyl, aryl, or deuterated aryl.

The term "silyl" refers to the group $R_3Si$—, where R is the same or different at each occurrence and is H, D, C1-20 alkyl, deuterated alkyl, fluoroalkyl, aryl, or deuterated aryl. In some embodiments, R is selected from C1-20 alkyl, deuterated alkyl, fluoroalkyl, aryl, deuterated aryl, and combinations thereof. In some embodiments, one or more carbons in an R alkyl group are replaced with Si.

The term "triplet energy" refers to the lowest excited triplet state of a material, in eV. Triplet energies are reported as positive numbers and represent the energy of the triplet state relative to the ground state, usually a singlet state.

Unless otherwise indicated, all groups can be unsubstituted or substituted. Unless otherwise indicated, all groups can be linear, branched or cyclic, where possible. In some embodiments, the substituents are selected from the group consisting of D, F, CN, alkyl, fluoroalkyl, aryl, heteroaryl, amino, silyl, alkoxy, aryloxy, fluoroalkoxy, siloxane, siloxy, deuterated alkyl, deuterated partially-fluorinated alkyl, deuterated aryl, deuterated heteroaryl, deuterated amino, deuterated silyl, deuterated alkoxy, deuterated aryloxy, deuterated fluoroalkoxy, deuterated siloxane, deuterated siloxy.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. An alternative embodiment of the disclosed subject matter hereof, is described as consisting essentially of certain features or elements, in which embodiment features or elements that would materially alter the principle of operation or the distinguishing characteristics of the embodiment are not present therein. A further alternative embodiment of the described subject matter hereof is described as consisting of certain features or elements, in which embodiment, or in insubstantial variations thereof, only the features or elements specifically stated or described are present.

Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Group numbers corresponding to columns within the Periodic Table of the elements use the "New Notation" convention as seen in the *CRC Handbook of Chemistry and Physics*, $81^{st}$ Edition (2000-2001).

Unless otherwise defined, all technical and scientific terms used herein have the same meaning as commonly understood by one of ordinary skill in the art to which this invention belongs. Although methods and materials similar or equivalent to those described herein can be used in the practice or testing of embodiments of the present invention, suitable methods and materials are described below. All publications, patent applications, patents, and other references mentioned herein are incorporated by reference in their entirety, unless a particular passage is cited In case of conflict, the present specification, including definitions, will control. In addition, the materials, methods, and examples are illustrative only and not intended to be limiting.

To the extent not described herein, many details regarding specific materials, processing acts, and circuits are conventional and may be found in textbooks and other sources within the organic light-emitting diode display, photodetector, photovoltaic, and semiconductive member arts.

2. COMPOUNDS OF FORMULAE I-V

Electron transport materials have been used as host materials in photoactive layers and in electron transport layers. Electron transport materials based on metal complexes of quinoline ligands, such as with Al, Ga, or Zr, have been used in these applications. However, there are several disadvantages. The complexes can have poor atmospheric stability when used as hosts. It is difficult to plasma clean fabricated parts employing such metal complexes. These materials also typically have low triplet energy.

Luminescent organometallic materials may emit from excited states having mixed singlet and triplet character and such materials are referred to herein as "phosphorescent". When organometallic phosphorescent materials are used in the light-emitting layer, the presence of materials having low triplet energy (<2.0 eV) leads to quenching of phosphorescent emission of >2.0 eV energy. This leads to decreased efficiency. In some embodiments, the compounds having Formula I, Formula II, Formula III, Formula IV, or Formula V have a triplet energy level greater than 2.1 eV; in some embodiments, greater than 2.3 eV; in some embodiments, greater than 2.5 eV; in some embodiments, greater than 2.7 eV; in some embodiments, greater than 2.8 eV. The triplet energy can either be calculated a priori, or be measured using pulse radiolysis or low temperature luminescence spectroscopy.

In some embodiments, the compounds are useful as solution processible electron dominated hosts for OLED devices or as electron transport materials suitable for n-doping in OLED devices having a thick electron transport layer. In some embodiments, devices made with the compounds can have lower operating voltage, higher efficiency and longer lifetimes. In some embodiments, the materials are useful in any printed electronics application, including photovoltaics and TFTs.

In some embodiments, the compound having at least one unit of Formula I is deuterated. In some embodiments, the compound is at least 20% deuterated; in some embodiments, at least 30% deuterated; in some embodiments, at least 40% deuterated; in some embodiments, at least 50% deuterated; in some embodiments, at least 60% deuterated; in some embodiments, at least 70% deuterated; in some embodiments, at least 80% deuterated; in some embodiments, at least 90% deuterated; in some embodiments, 100% deuterated.

The compounds described herein are azacarbazoles having one nitrogen in position 1, 2, 3, or 4, where the numbering is shown below.

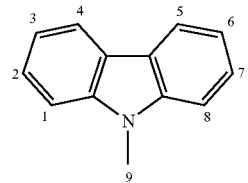

The compounds have Formula I

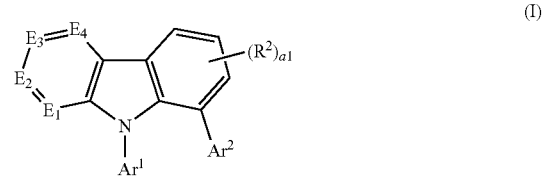

(I)

wherein:
  $E_1$-$E_4$ are selected from the group consisting of CH, CD, $CR^1$, and
    N, where one and only one of $E_1$-$E_4$ is N;
  $Ar^1$ is selected from the group consisting of an N-heterocycle and a deuterated N-heterocycle;
  $Ar^2$ is selected from the group consisting of hydrocarbon aryl, heteroaryl, diarylamino, N-carbazolyl, substituted derivatives thereof, and deuterated analogs thereof;
  $R^1$ and $R^2$ are the same or different at each occurrence and are selected from the group consisting of D, alkyl, silyl, germyl, hydrocarbon aryl, heteroaryl, deuterated alkyl, deuterated silyl, deuterated germyl, deuterated hydrocarbon aryl, and deuterated heteroaryl; and
  a1 is an integer from 0-3.

In Formula I, one of $E_1$-$E_4$ is N and the remaining $E_1$-$E_4$ groups are CH, CD, or $CR^1$.

In some embodiments, the compound having Formula I is deuterated. In some embodiments, the compound is at least 10% deuterated; in some embodiments, at least 20% deuterated; in some embodiments, at least 30% deuterated; in some embodiments, at least 40% deuterated; in some embodiments, at least 50% deuterated; in some embodiments, at least 60% deuterated; in some embodiments, at least 70% deuterated; in some embodiments, at least 80% deuterated; in some embodiments, at least 90% deuterated; in some embodiments, 100% deuterated.

In some embodiments of Formula I, $E_1$=N.
In some embodiments of Formula I, $E_2$=N.
In some embodiments of Formula I, $E_3$=N.
In some embodiments of Formula I, $E_4$=N.
In some embodiments of Formula I, $E_1$=N.
In some embodiments of Formula I, $E_2$=N.
In some embodiments of Formula I, $E_3$=N.
In some embodiments of Formula I, $E_4$=N.

In some embodiments of Formula I, one of $E_1$-$E_4$ is N and the remaining $E_1$-$E_4$ groups are CH or CD.

In some embodiments of Formula I, at least one of $E_1$-$E_4$ is $CR^1$.

In some embodiments of Formula I, at least one of $E_1$-$E_4$ is $CR^1$, and $R^1$ is selected from the group consisting of alkyl, silyl, germyl and deuterated analogs thereof, having 1-12 carbons.

In some embodiments of Formula I, at least one of $E_1$-$E_4$ is $CR^1$, and $R^1$ is a hydrocarbon aryl or deuterated hydrocarbon aryl, having 6-18 ring carbons.

In Formula I, $Ar^1$ is selected from the group consisting of an N-heterocycle and a deuterated N-heterocycle. The N-heterocycle is bonded through a ring carbon. In some embodiments, the nitrogen-containing ring of the N-heterocycle is bonded directly to the nitrogen at position 9 of the azacarbazole.

Examples of N-heterocycles include, but are not limited to, those shown below.

where Y is an aryl group. The group can be bonded at any of the carbon positions available. Deuterated analogs of the above groups may also be used.

In some embodiments, the N-heterocycle is substituted. Exemplary substituents include D, alkyl, silyl, germyl, hydrocarbon aryl, alkylaryl, silylaryl, heteroaryl, deuterated alkyl, deuterated silyl, deuterated germyl, deuterated hydrocarbon aryl, deuterated alkylaryl, deuterated silylaryl, deuterated heteroaryl, and combinations thereof.

In some embodiments, the N-heterocycle is substituted with a substituent selected from the group consisting of silyl, aryl, alkylaryl, silylaryl, N-heteroaryl, and deuterated analogs thereof.

In some embodiments, the N-heterocycle is pyridine, pyrimidine, triazine, a substituted derivative thereof, or a deuterated analog thereof.

In some embodiments of Formula I, $Ar^2$ is a hydrocarbon aryl or deuterated hydrocarbon aryl having 6-18 ring carbons.

In some embodiments of Formula I, $Ar^2$ is substituted. Exemplary substituents include D, alkyl, silyl, germyl, hydrocarbon aryl, alkylaryl, silylaryl, heteroaryl, deuterated alkyl, deuterated silyl, deuterated germyl, deuterated hydrocarbon aryl, deuterated alkylaryl, deuterated silylaryl, deuterated heteroaryl, and combinations thereof.

In some embodiments of Formula I, $Ar^2$ is substituted with at least one substituent selected from the group consisting of silyl, aryl, alkylaryl, silylaryl, N-heteroaryl, deuterated analogs thereof, and combinations thereof.

In some embodiments of Formula I, $Ar^2$ is a diarylamino group or deuterated analog thereof.

In some embodiments of Formula I, $Ar^2$ is a diarylamino group having aryl groups which are the same or different and which are selected from the group consisting of phenyl, biphenyl, terphenyl, substituted derivatives thereof, and deuterated analogs thereof. Exemplary substituents include D, alkyl, silyl, germyl, hydrocarbon aryl, alkylaryl, silylaryl, heteroaryl, deuterated alkyl, deuterated silyl, deuterated germyl, deuterated hydrocarbon aryl, deuterated alkylaryl, deuterated silylaryl, deuterated heteroaryl, and combinations thereof.

In some embodiments of Formula I, $Ar^2$ is an unsubstituted or substituted N-carbazolyl group or deuterated analog thereof.

In some embodiments of Formula I, $Ar^2$ is a substituted N-carbazolyl group or deuterated analog thereof. Exemplary substituents include alkyl, silyl, germyl, and deuterated analogs thereof.

In some embodiments of Formula I, a1=0.
In some embodiments of Formula I, a1=1.
In some embodiments of Formula I, a1=2.
In some embodiments of Formula I, a1=3.
In some embodiments of Formula I, a1>0.
In some embodiments of Formula I, a1>0 and at least one $R^2$ is D.
In some embodiments of Formula I, a1>0 and at least one $R^2$ is selected from the group consisting of alkyl, silyl, germyl and deuterated analogs thereof, having 1-12 carbons.
In some embodiments of Formula I, a1>0 and at least one $R^2$ is an aryl or deuterated aryl having 6-18 ring carbons.
In some embodiments of Formula I, a1 is 0 or 1.

Any of the above embodiments of Formula I can be combined with one or more of the other embodiments, so long as they are not mutually exclusive. For example, the embodiment in which a1=1 can be combined with the embodiment where $R^2$ is an aryl or deuterated aryl having 6-18 ring carbons and with the embodiment where $Ar^2$ is a substituted N-carbazolyl group or deuterated analog thereof. The same is true for the other non-mutually-exclusive embodiments discussed above. The skilled person would understand which embodiments were mutually exclusive and would thus readily be able to determine the combinations of embodiments that are contemplated by the present application.

In some embodiments of Formula I, the compound has Formula II (II)

wherein:
$Ar^1$ is selected from the group consisting of an N-heterocycle and a deuterated N-heterocycle;

Ar² is selected from the group consisting of hydrocarbon aryl, heteroaryl, diarylamino, N-carbazolyl, substituted derivatives thereof, and deuterated analogs thereof;

R¹ and R² are the same or different at each occurrence and are selected from the group consisting of D, alkyl, silyl, germyl, hydrocarbon aryl, heteroaryl, deuterated alkyl, deuterated silyl, deuterated germyl, deuterated hydrocarbon aryl, and deuterated heteroaryl; and a and a1 are the same or different and are integers from 0-3.

In some embodiments of Formula II, a=0.

In some embodiments of Formula II, a=1.

In some embodiments of Formula II, a=2.

In some embodiments of Formula II, a=3.

In some embodiments of Formula II, a>0.

In some embodiments of Formula II, a>0 and at least one R¹ is D.

In some embodiments of Formula II, a>0 and at least one R¹ is selected from the group consisting of alkyl, silyl, germyl, and deuterated analogs thereof, having 1-12 carbons.

In some embodiments of Formula II, a>0 and at least one R¹ is an aryl or deuterated aryl having 6-18 ring carbons.

In some embodiments of Formula II, a=0 or 1.

All of the embodiments for deuteration, Ar¹, Ar², R¹, R², a and a1 described above for Formula I apply equally to Formula II.

Any of the above embodiments of Formula II can be combined with one or more of the other embodiments, so long as they are not mutually exclusive.

In some embodiments of Formula I, the compound has Formula III

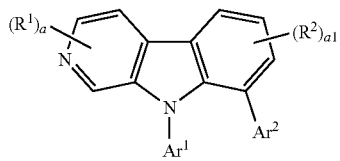

(III)

wherein:
Ar¹ is selected from the group consisting of an N-heterocycle and a deuterated N-heterocycle;

Ar² is selected from the group consisting of hydrocarbon aryl, heteroaryl, diarylamino, N-carbazolyl, substituted derivatives thereof, and deuterated analogs thereof;

R¹ and R² are the same or different at each occurrence and are selected from the group consisting of D, alkyl, silyl, germyl, hydrocarbon aryl, heteroaryl, deuterated alkyl, deuterated silyl, deuterated germyl, deuterated hydrocarbon aryl, and deuterated heteroaryl; and a and a1 are the same or different and are integers from 0-3.

All of the embodiments for deuteration, Ar¹, Ar², R¹, R², a and a1 described above for Formula II apply equally to Formula III.

Any of the above embodiments of Formula III can be combined with one or more of the other embodiments, so long as they are not mutually exclusive.

In some embodiments of Formula I, the compound has Formula IV

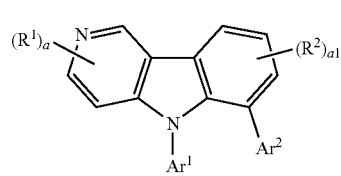

(IV)

wherein:
Ar¹ is selected from the group consisting of an N-heterocycle and a deuterated N-heterocycle;

Ar² is selected from the group consisting of hydrocarbon aryl, heteroaryl, diarylamino, N-carbazolyl, substituted derivatives thereof, and deuterated analogs thereof;

R¹ and R² are the same or different at each occurrence and are selected from the group consisting of D, alkyl, silyl, germyl, hydrocarbon aryl, heteroaryl, deuterated alkyl, deuterated silyl, deuterated germyl, deuterated hydrocarbon aryl, and deuterated heteroaryl; and a and a1 are the same or different and are integers from 0-3.

All of the embodiments for deuteration, Ar¹, Ar², R¹, R², a and a1 described above for Formula II apply equally to Formula IV.

Any of the above embodiments of Formula IV can be combined with one or more of the other embodiments, so long as they are not mutually exclusive.

In some embodiments of Formula I, the compound has Formula V

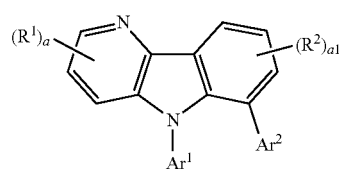

(V)

wherein:
Ar¹ is selected from the group consisting of an N-heterocycle and a deuterated N-heterocycle;

Ar² is selected from the group consisting of hydrocarbon aryl, heteroaryl, diarylamino, N-carbazolyl, substituted derivatives thereof, and deuterated analogs thereof;

R¹ and R² are the same or different at each occurrence and are selected from the group consisting of D, alkyl, silyl, germyl, hydrocarbon aryl, heteroaryl, deuterated alkyl, deuterated silyl, deuterated germyl, deuterated hydrocarbon aryl, and deuterated heteroaryl; and a and a1 are the same or different and are integers from 0-3.

All of the embodiments for deuteration, Ar¹, Ar², R¹, R², a and a1 described above for Formula II apply equally to Formula V.

Any of the above embodiments of Formula V can be combined with one or more of the other embodiments, so long as they are not mutually exclusive.

In some embodiments, the compound having Formula II, Formula III, Formula IV, or Formula V is deuterated. In some embodiments, the compound is at least 20% deuterated; in some embodiments, at least 30% deuterated; in some embodiments, at least 40% deuterated; in some embodiments, at least 50% deuterated; in some embodiments, at least 60% deuterated; in some embodiments, at least 70% deuterated; in some embodiments, at least 80% deuterated; in some embodiments, at least 90% deuterated; in some embodiments, 100% deuterated.

Some examples of compounds having Formula I are shown below.

Compound A1

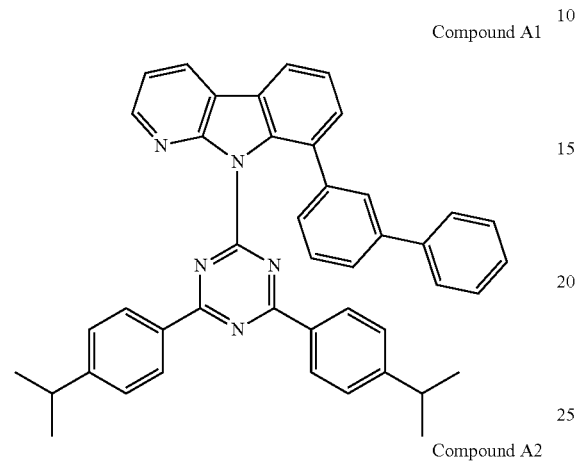

Compound A2

Compound A3

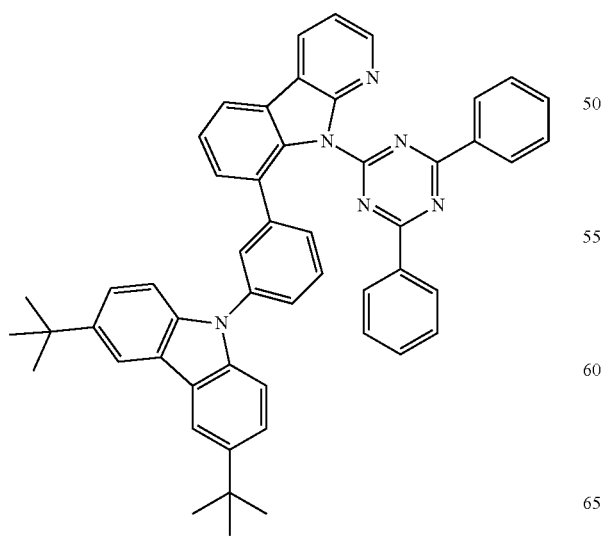

-continued

Compound A4

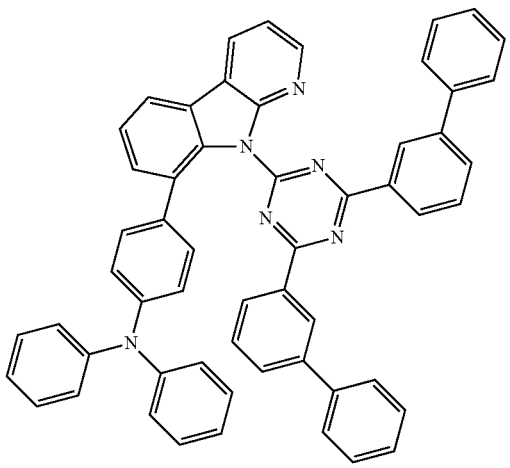

Compound A5

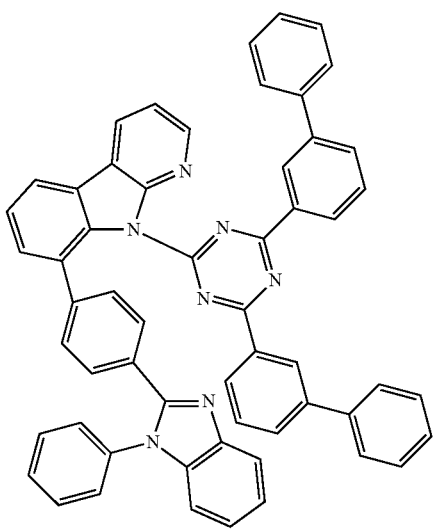

Compound A6

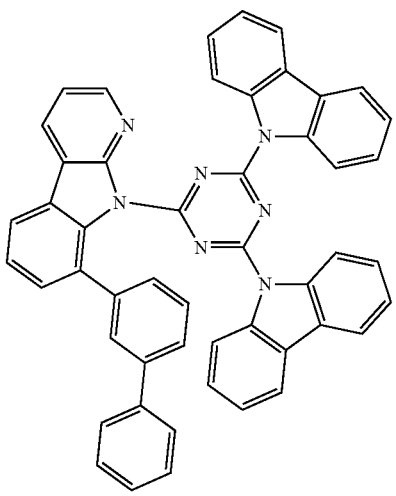

-continued
Compound A7
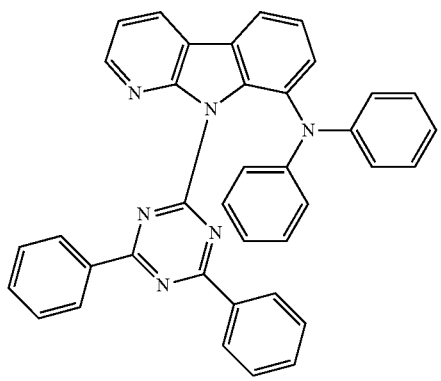
Compound A8
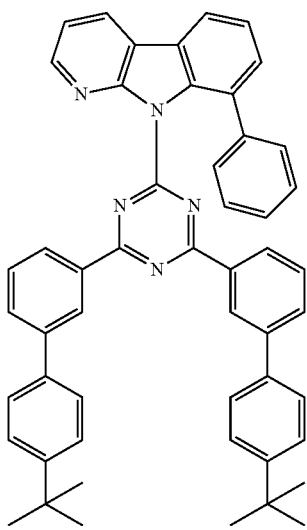
Compound A9
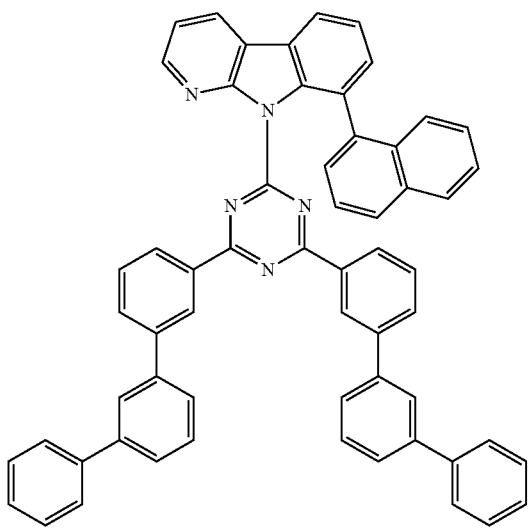
-continued
Compound A10
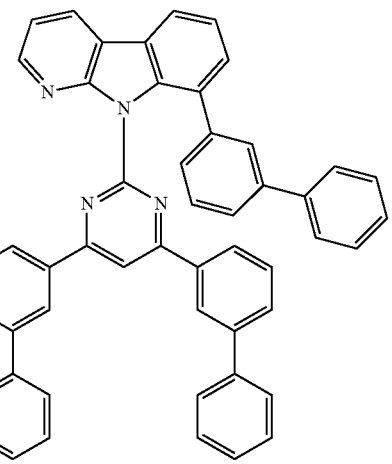
Compound A11
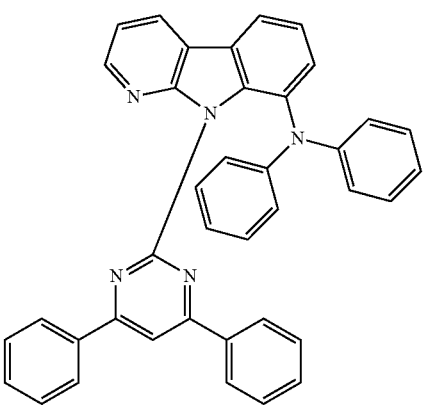
Compound A12
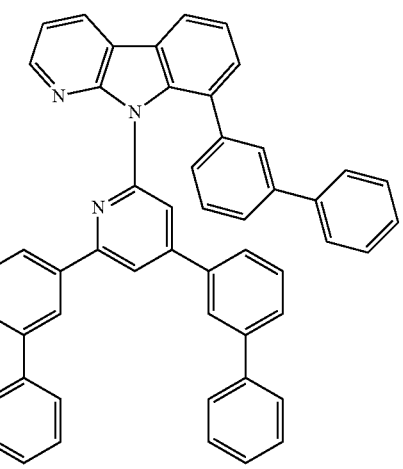
3. SYNTHESIS
Carbazole compounds having aryl substituents at the 9-position and aryl or diarylamino substituents at the 1-position are known, where the numbering is shown below.

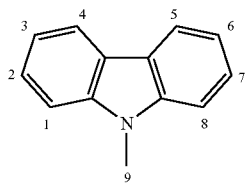

The synthesis generally starts with 1-halocarbazole. The aryl or diarylamino substituents are added in two steps: (1) the 9-aryl substituent is added as a chloro derivative in the presence of a strong base such as NaH; and (2) either (i) the 1-aryl substituent is added as a boronic acid derivative or boronate ester derivative in the presence of a metal catalyst, such as a Pd(0) catalyst; or (ii) the 1-diarylamino substituent is added as a secondary amine in the presence of a metal catalyst, such as a Pd(0) catalyst. The steps (1) and (2) can be carried out in either order, and both the intermediate and final products are typically treated with aqueous or other protic solvents.

The compounds having Formula II,

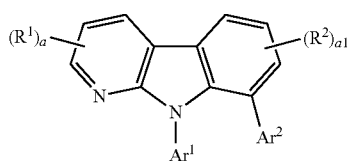

(II)

as described in detail above, have a core 1-azacarbazole group, where the numbering is shown below.

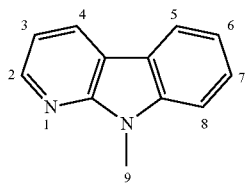

There is an aryl or diarylamino substituent at the 8-position and an N-heteroaryl at the 9-position.

The compound 8-chloro-1-azacarbazole is commercially available. However, using the synthetic route described above for carbazole does not result in the compound of Formula II.

Surprisingly, it has been discovered that the reaction of the 1-azacarbazole with the chloroderivative of the N-heterocycle results in addition of the N-heterocycle to the 1-aza nitrogen.

If the reaction takes place after the substituent is added at the 8-position, Compound II-A is formed.

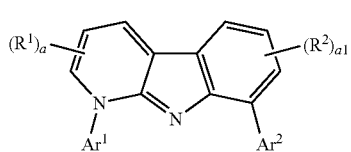

(II-A)

where Ar¹, Ar², R¹, R², a and a1 are as defined above for Formula I.

If the reaction takes place before addition of the substituent at the 8-position, Compound II-B is formed.

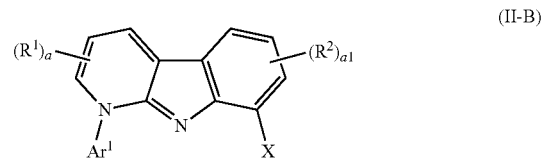

(II-B)

where X is halide and Ar', R¹, R², a and a1 are as defined above for Formula I.

If either of Compound II-A or Compound II-B is exposed to water, alcohol, or other compounds with available hydrogen ions, the reaction is reversed to form a complex mixture of starting materials and acids.

Suprisingly and unexpectedly, the Compound of Formula II can be formed by thermal rearrangement of Compound II-A (Process A) or Compound II-B (Process B).

Process A is illustrated schematically below with Compound II-A, where Ar²ᵃ represents an aryl substituent, Ar²ᵇH represents a diarylamino or N-carbazolyl compound, where the H is bonded to N, Q represents an N-heterocycle group, and X represents halide.

Scheme A-1

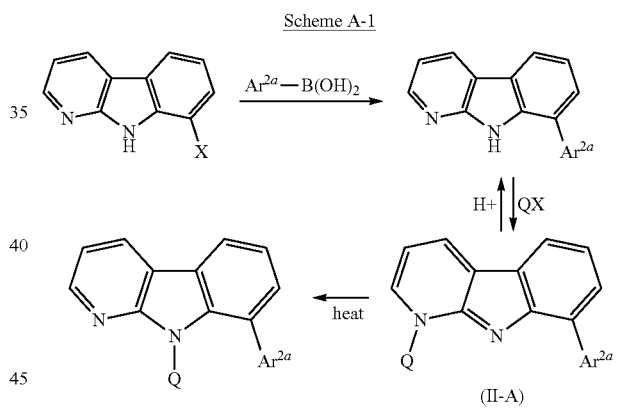

Scheme A-2

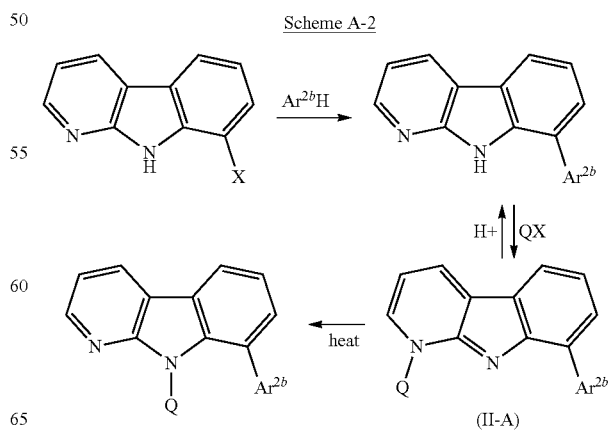

With Process A, there is provided a process of making a Z-azacarbazole derivative, where Z=1, 2, 3, or 4, comprising the steps, in order, in an inert atmosphere:

(1) providing a Z-aza-8-halo-carbazole compound;
(2) either
    (a) treating the compound from step (1) with an aryl-boronic acid derivative or aryl-boronate ester derivative in the presence of a zerovalent metal catalyst;
    or
    (b) treating the compound from step (1) with a diarylamine or carbazole in the presence of a zerovalent metal catalyst and an anhydrous strong base;
(3) treating the reaction product of step (2) with a halide derivative of an N-heterocycle in the presence of an anhydrous strong base; and
(4) heating the reaction product of Step (3) to a temperature of 200° C. or greater to form a Z-azacarbazole compound having a substituent at position 8 which is an aryl, diarylamino, or N-carbazolyl group and a substituent at position 9 which is an N-heterocycle.

Process B is illustrated schematically below with Compound II-B, where $Ar^{2a}$, $Ar^{2b}H$, Q, and X are as defined above.

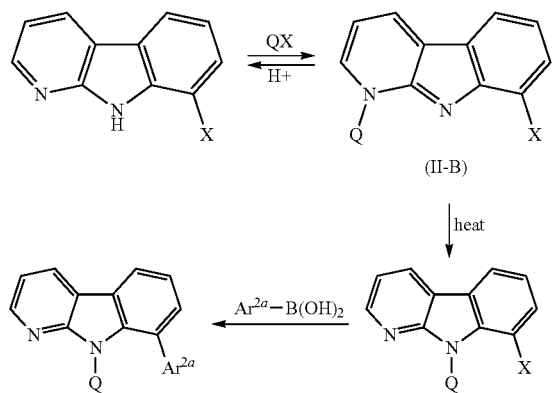

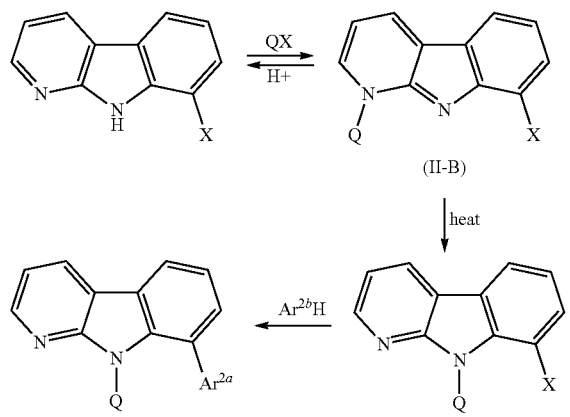

With Process B, there is provided a process of making a Z-azacarbazole derivative, where Z=1, 2, 3, or 4, comprising the steps, in order, in an inert atmosphere:

(1) providing a Z-aza-8-halo-carbazole compound;
(2) treating the compound from step (1) with a halide derivative of an N-heterocycle in the presence of an anhydrous strong base;
(3) heating the reaction product of Step (2) to a temperature of 200° C. or greater; and
(4) either
    (a) treating the reaction product of step (3) with an aryl-boronic acid derivative or aryl-boronate ester derivative in the presence of a zerovalent metal catalyst to form a Z-azacarbazole compound having a substituent at position 8 which is an aryl group and a substituent at position 9 which is an N-heterocycle;
    or
    (b) treating the compound from step (1) with a diarylamine or carbazole compound in the presence of a zerovalent metal catalyst and an anhydrous strong base to form a Z-azacarbazole compound having a substituent at position 8 which is a diarylamino or N-carbazolyl group and a substituent at position 9 which is an N-heterocycle.

In either Process A or Process B, the Z-aza-8-halo-carbazole compound can have no additional substituents or have additional substituents $R^1$ and/or $R^2$, as discussed above for Formula I.

In either Process A or Process B, the aryl group can be unsubstituted or have additional substituents, as discussed above for $Ar^2$ in Formula I.

In either Process A or Process B, the diarylamino compound is a secondary amine having an N—H moiety. The diarylamino compound can be unsubstituted or have additional substituents, as discussed above for $Ar^2$ in Formula I.

In either Process A or Process B, the carbazolyl compound has no substituents on the carbazole nitrogen, and thus has an N—H moiety. The carbazolyl compound can be unsubstituted or have additional substituents, as discussed above for $Ar^2$ in Formula I.

In either Process A or Process B, the N-heterocycle can be unsubstituted or have additional substituents, as discussed above for Formula I.

In some embodiments of either Process A or Process B, Z=1.

In some embodiments of either Process A or Process B, Z=2.

In some embodiments of either Process A or Process B, Z=3.

In some embodiments of either Process A or Process B, Z=4.

In some embodiments of either Process A or Process B, the zerovalent metal catalyst is a Pd(0) compound. Pd(0) catalysis is well known. Exemplary compounds include $Pd(dba)_2$ and $Pd_2(dba)_3$, where dba=bis(dibenzylideneacetone).

In some embodiments of either Process A or Process B, the anhydrous strong base is a metal hydride, such as NaH.

In some embodiments of either Process A or Process B, the anhydrous strong base is an alkali metal amide, such as lithium diisopropylamide or lithium bis(trimethylsilyl)amide.

In some embodiments of either Process A or Process B, the heating step is carried out at a temperature of 200-250° C.; in some embodiments, 210-230° C.

In some embodiments of either Process A or Process B, the heating step is carried out for at least 15 minutes; in some embodiments, at least 30 minutes. In some embodiments, the heating step is carried out for a time of 15 minutes to 10 hours; in some embodiments, 30 minutes to 5 hours; in some embodiments 1-4 hours.

Detailed synthetic steps are given in the examples.

The deuterated analog compounds can be prepared in a similar manner using deuterated precursor materials or, more generally, by treating the non-deuterated compound with deuterated solvent, such as d6-benzene, in the presence of a Lewis acid H/D exchange catalyst, such as trifluoromethanesulfonic acid, aluminum trichloride or ethyl aluminum dichloride. Deuteration reactions have also been described in copending application published as PCT application WO 2011-053334.

The compounds described herein can be formed into films using liquid deposition techniques. This is further illustrated in the examples.

Alternatively, they can be formed into films using vapor deposition techniques.

4. ELECTROACTIVE COMPOSITION

There is also provided a composition comprising (a) a host compound having Formula I and (b) a dopant capable of electroluminescence having an emission maximum between 380 and 750 nm. The compounds of Formula I are useful as host materials for photoactive materials. The compounds can be used alone, or in combination with another host material. The compounds of Formula I can be used as a host for dopants with any color of emission. In some embodiments, the compound as used as hosts for organometallic electroluminescent material.

In some embodiments, the composition comprises (a) a host compound having Formula I and (b) a photoactive dopant capable of electroluminescence having an emission maximum between 380 and 750 nm. In some embodiments, the composition consists essentially of (a) a host compound having Formula I and (b) a photoactive dopant capable of electroluminescence having an emission maximum between 380 and 750 nm. In some embodiments, the composition comprises (a) a host compound having Formula I, (b) a photoactive dopant capable of electroluminescence having an emission maximum between 380 and 750 nm, and (c) a second host material. In some embodiments, the composition comprises (a) a host compound having Formula I, (b) a photoactive dopant capable of electroluminescence having an emission maximum between 380 and 750 nm, and (c) a second host material.

In some embodiments, the host compound has Formula II.

In some embodiments, the host compound has Formula III.

In some embodiments, the host compound has Formula IV.

In some embodiments, the host compound has Formula V.

The amount of dopant present in the composition is generally in the range of 3-20% by weight, based on the total weight of the composition; in some embodiments, 5-15% by weight. When a second host is present, the ratio of first host having Formula I to second host is generally in the range of 1:20 to 20:1; in some embodiments, 5:15 to 15:5. In some embodiments, the first host material having Formula I is at least 50% by weight of the total host material; in some embodiments, at least 70% by weight.

Electroluminescent ("EL") materials which can be used as a dopant include, but are not limited to, small molecule organic luminescent compounds, luminescent metal complexes, conjugated polymers, and mixtures thereof. Examples of small molecule luminescent organic compounds include, but are not limited to, chrysenes, pyrenes, perylenes, rubrenes, coumarins, anthracenes, thiadiazoles, benzofluorenes, derivatives thereof, and mixtures thereof. Examples of metal complexes include, but are not limited to, metal chelated oxinoid compounds and cyclometallated complexes of metals such as iridium and platinum. Examples of conjugated polymers include, but are not limited to poly(phenylenevinylenes), polyfluorenes, poly (spirobifluorenes), polythiophenes, poly(p-phenylenes), copolymers thereof, and mixtures thereof.

Examples of red light-emitting materials include, but are not limited to, complexes of Ir having phenylquinoline or phenylisoquinoline ligands, periflanthenes, fluoranthenes, and perylenes. Red light-emitting materials have been disclosed in, for example, U.S. Pat. No. 6,875,524, and published US application 2005-0158577.

Examples of green light-emitting materials include, but are not limited to, complexes of Ir having phenylpyridine ligands, bis(diarylamino)anthracenes, and polyphenylenevinylene polymers. Green light-emitting materials have been disclosed in, for example, published PCT application WO 2007/021117.

Examples of blue light-emitting materials include, but are not limited to, complexes of Ir having phenylpyridine or phenylimidazole ligands, diarylanthracenes, diaminochrysenes, diaminopyrenes, diaminobenzofluorenes, and polyfluorene polymers. Blue light-emitting materials have been disclosed in, for example, U.S. Pat. No. 6,875,524, and published US applications 2007-0292713 and 2007-0063638.

In some embodiments, the dopant is an organometallic complex. In some embodiments, the organometallic complex is cyclometallated. By "cyclometallated" it is meant that the complex contains at least one ligand which bonds to the metal in at least two points, forming at least one 5- or 6-membered ring with at least one carbon-metal bond. In some embodiments, the metal is iridium or platinum. In some embodiments, the organometallic complex is electrically neutral and is a tris-cyclometallated complex of iridium having the formula $IrL_3$ or a bis-cyclometallated complex of iridium having the formula $IrL_2Y$. In some embodiments, L is a monoanionic bidentate cyclometalating ligand coordinated through a carbon atom and a nitrogen atom. In some embodiments, L is an aryl N-heterocycle, where the aryl is phenyl or napthyl, and the N-heterocycle is pyridine, quinoline, isoquinoline, diazine, pyrrole, pyrazole or imidazole. In some embodiments, Y is a monoanionic bidentate ligand. In some embodiments, L is a phenylpyridine, a phenylquinoline, or a phenylisoquinoline. In some embodiments, Y is a β-dienolate, a diketimine, a picolinate, or an N-alkoxypyrazole. The ligands may be unsubstituted or substituted with F, D, alkyl, perfluororalkyl, alkoxyl, alkylamino, arylamino, CN, silyl, fluoroalkoxy or aryl groups.

In some embodiments, the dopant is a cyclometalated complex of iridium or platinum. Such materials have been disclosed in, for example, U.S. Pat. No. 6,670,645 and Published PCT Applications WO 03/063555, WO 2004/016710, and WO 03/040257.

In some embodiments, the dopant is a complex having the formula

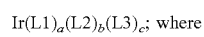

$Ir(L1)_a(L2)_b(L3)_c$; where

L1 is a monoanionic bidentate cyclometalating ligand coordinated through carbon and nitrogen;

L2 is a monoanionic bidentate ligand which is not coordinated through a carbon;

L3 is a monodentate ligand;

a is 1-3;

b and c are independently 0-2; and a, b, and c are selected such that the iridium is hexacoordinate and the complex is electrically neutral.

Some examples of formulae include, but are not limited to, $Ir(L1)_3$; $Ir(L1)_2(L2)$; and $Ir(L1)_2(L3)(L3')$, where L3 is anionic and L3' is nonionic.

Examples of L1 ligands include, but are not limited to phenylpyridines, phenylquinolines, phenylpyrimidines, phenylpyrazoles, thienylpyridines, thienylquinolines, and thienylpyrimidines. As used herein, the term "quinolines" includes "isoquinolines" unless otherwise specified. The fluorinated derivatives can have one or more fluorine substituents. In some embodiments, there are 1-3 fluorine substituents on the non-nitrogen ring of the ligand.

Monoanionic bidentate ligands, L2, are well known in the art of metal coordination chemistry. In general these ligands have N, O, P, or S as coordinating atoms and form 5- or 6-membered rings when coordinated to the iridium. Suitable coordinating groups include amino, imino, amido, alkoxide, carboxylate, phosphino, thiolate, and the like. Examples of suitable parent compounds for these ligands include β-dicarbonyls (β-enolate ligands), and their N and S analogs; amino carboxylic acids (aminocarboxylate ligands); pyridine carboxylic acids (iminocarboxylate ligands); salicylic acid derivatives (salicylate ligands); hydroxyquinolines (hydroxyquinolinate ligands) and their S analogs; and phosphinoalkanols (phosphinoalkoxide ligands).

Monodentate ligand L3 can be anionic or nonionic. Anionic ligands include, but are not limited to, H⁻ ("hydride") and ligands having C, O or S as coordinating atoms. Coordinating groups include, but are not limited to alkoxide, carboxylate, thiocarboxylate, dithiocarboxylate, sulfonate, thiolate, carbamate, dithiocarbamate, thiocarbazone anions, sulfonamide anions, and the like. In some cases, ligands listed above as L2, such as β-enolates and phosphinoakoxides, can act as monodentate ligands. The monodentate ligand can also be a coordinating anion such as halide, cyanide, isocyanide, nitrate, sulfate, hexahaloantimonate, and the like. These ligands are generally available commercially.

The monodentate L3 ligand can also be a non-ionic ligand, such as CO or a monodentate phosphine ligand.

In some embodiments, one or more of the ligands has at least one substituent selected from the group consisting of F and fluorinated alkyls.

The iridium complex dopants can be made using standard synthetic techniques as described in, for example, U.S. Pat. No. 6,670,645.

In some embodiments, the dopant is a small organic luminescent compound. In some embodiments, the dopant is selected from the group consisting of a non-polymeric spirobifluorene compound and a fluoranthene compound.

In some embodiments, the dopant is a compound having aryl amine groups. In some embodiments, the photoactive dopant is selected from the formulae below:

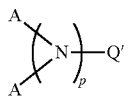 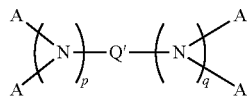

-continued

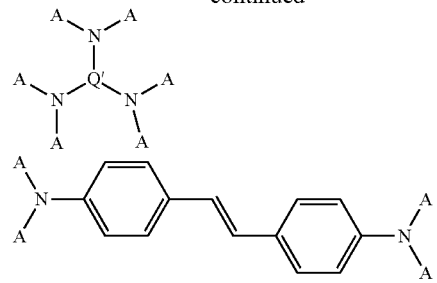

where:

A is the same or different at each occurrence and is an aromatic group having from 3-60 carbon atoms;

Q' is a single bond or an aromatic group having from 3-60 ring carbon atoms;

p and q are independently an integer from 1-6.

In some embodiments of the above formula, at least one of A and Q' in each formula has at least three condensed rings. In some embodiments, p and q are equal to 1.

In some embodiments, Q' is a styryl or styrylphenyl group.

In some embodiments, Q' is an aromatic group having at least two condensed rings. In some embodiments, Q' is selected from the group consisting of naphthalene, anthracene, chrysene, benzofluorene, pyrene, tetracene, xanthene, perylene, coumarin, rhodamine, quinacridone, and rubrene.

In some embodiments, A is selected from the group consisting of phenyl, biphenyl, tolyl, naphthyl, naphthylphenyl, and anthracenyl groups.

In some embodiments, the dopant has the formula below:

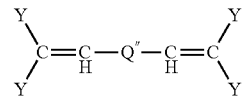

where:

Y is the same or different at each occurrence and is an aromatic group having 3-60 carbon atoms;

Q" is an aromatic group, a divalent triphenylamine residue group, or a single bond.

In some embodiments, the dopant is an aryl acene. In some embodiments, the dopant is a non-symmetrical aryl acene.

In some embodiments, the photoactive dopant is a chrysene derivative. The term "chrysene" is intended to mean 1,2-benzophenanthrene. In some embodiments, the photoactive dopant is a chrysene having aryl substituents. In some embodiments, the photoactive dopant is a chrysene having arylamino substituents. In some embodiments, the photoactive dopant is a chrysene having two different arylamino substituents. In some embodiments, the chrysene derivative has a deep blue emission.

In some embodiments, the compound having Formula I is used with an additional host material. In some embodiments, the compound having Formula I is not used as a host in the photoactive layer. Examples of other types of hosts which can be used alone or as a second host in combination with the compounds having Formula I, include, but are not limited to, chrysenes, phenanthrenes, triphenylenes, phenanthrolines, triazines, naphthalenes, anthracenes, quinolines, isoquinolines, quinoxalines, phenylpyridines, carbazoles, indolocarbazoles, indoloindoles, furans, benzofurans, dibenzofurans, benzodifurans, metal quinolinate complexes, substituted derivatives thereof, and deuterated analogs thereof.

In some embodiments, the compound having Formula I is used as an electron transport material in an electron transport layer of a device.

5. ORGANIC ELECTRONIC DEVICE

Organic electronic devices that may benefit from having one or more layers comprising the compounds described herein include, but are not limited to, (1) devices that convert electrical energy into radiation (e.g., a light-emitting diode, light-emitting diode display, light-emitting luminaire, or diode laser), (2) devices that detect signals through electronics processes (e.g., photodetectors, photoconductive cells, photoresistors, photoswitches, phototransistors, phototubes, IR detectors), (3) devices that convert radiation into electrical energy, (e.g., a photovoltaic device or solar cell), (4) devices that convert light of one wavelength to light of a longer wavelength, (e.g., a down-converting phosphor device); and (5) devices that include one or more electronic components that include one or more organic semi-conductor layers (e.g., a transistor or diode). The compounds of the invention often can be useful in applications such as oxygen sensitive indicators and as luminescent indicators in bioassays.

In one embodiment, an organic electronic device comprises at least one layer comprising the compound having Formula I as discussed above.

The present invention also relates to an electronic device comprising at least one electroactive layer positioned between two electrical contact layers, wherein the at least one electroactive layer of the device includes a compound having Formula I.

One illustration of an organic electronic device structure including a compound having Formula I is shown in FIG. 1. The device 100 has a first electrical contact layer, an anode layer 110 and a second electrical contact layer, a cathode layer 160, and a photoactive layer 140 between them. Additional layers may optionally be present. Adjacent to the anode may be a hole injection layer 120, sometimes referred to as a buffer layer. Adjacent to the hole injection layer may be a hole transport layer 130, including hole transport material. Adjacent to the cathode may be an electron transport layer 150, including an electron transport material. As an option, devices may use one or more additional hole injection or hole transport layers (not shown) next to the anode 110 and/or one or more additional electron injection or electron transport layers (not shown) next to the cathode 160. Layers 120 through 150 are individually and collectively referred to as the organic active layers.

Figure 2:
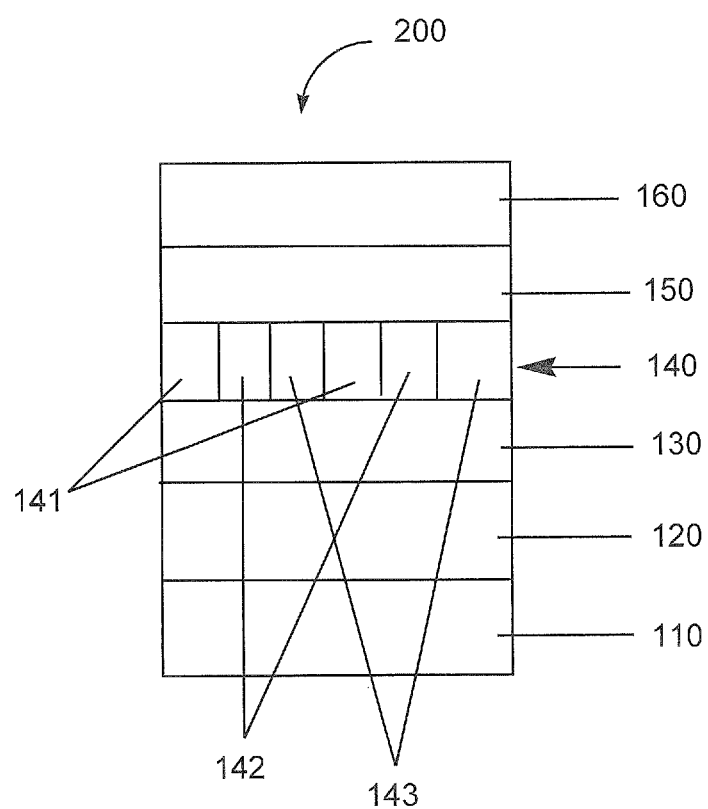
FIG. 2 includes an illustration of another example of an organic electronic device.

In some embodiments, in order to achieve full color, the light-emitting layer is pixellated, with subpixel units for each of the different colors. An illustration of a pixellated device including a compound having Formula I is shown in FIG. 2. The device 200 has anode 110, hole injection layer 120, hole transport layer 130, photoactive layer 140, electron transport layer 150, and cathode 160. The photoactive layer is divided into subpixels 141, 142, 143, which are repeated across the layer. In some embodiments, the subpixels represent red, blue and green color emission. Although three different subpixel units are depicted in FIG. 2, two or more than three subpixel units may be used.

The different layers will be discussed further herein with reference to FIG. 1. However, the discussion applies to FIG. 2 and other configurations as well.

In one embodiment, the different layers have the following range of thicknesses: anode, 500-5000 Å, in one embodiment 1000-2000 Å; hole injection layer, 50-2000 Å, in one embodiment 200-1000 Å; hole transport layer, 50-2000 Å, in one embodiment 200-1000 Å; electroactive layer, 10-2000 Å, in one embodiment 100-1000 Å; layer, 50-2000 Å, in one embodiment 100-1000 Å; cathode, 200-10000 Å, in one embodiment 300-5000 Å. The location of the electron-hole recombination zone in the device, and thus the emission spectrum of the device, can be affected by the relative thickness of each layer. The desired ratio of layer thicknesses will depend on the exact nature of the materials used. In some embodiments, the devices have additional layers to aid in processing or to improve functionality.

Depending upon the application of the device, the photoactive layer can be a light-emitting layer that is activated by an applied voltage (such as in a light-emitting diode or light-emitting electrochemical cell), or a layer of material that responds to radiant energy and generates a signal with or without an applied bias voltage (such as in a photodetector). Examples of photodetectors include photoconductive cells, photoresistors, photoswitches, phototransistors, and phototubes, and photovoltaic cells, as these terms are described in Markus, John, *Electronics and Nucleonics Dictionary*, 470 and 476 (McGraw-Hill, Inc. 1966). Devices with light-emitting layers may be used to form displays or for lighting applications, such as white light luminaires.

One or more of the new compounds described herein may be present in one or more of the electroactive layers of a device.

In some embodiments, the new compounds having Formula I are useful as host materials for photoactive dopant materials in photoactive layer. It has been found that when these compounds are used by themselves or in conjunction with other cohosts, they can provide improved efficiency and lifetime in OLED devices. It has been discovered through calculations that these compounds have high triplet energies and HOMO and LUMO levels appropriate for charge transport, making them excellent host materials for organometallic emitters.

In some embodiments, the new compounds are useful as electron transport materials in layer.

In some embodiments, the new compounds are present as a host in the photoactive layer and also present as an electron transport material in layer.

Photoactive Layer

In some embodiments, the photoactive layer comprises the electroactive composition described above.

In some embodiments, the dopant is an organometallic material. In some embodiments, the organometallic material is a complex of Ir or Pt. In some embodiments, the organometallic material is a cyclometallated complex of Ir.

In some embodiments, the photoactive layer comprises (a) a host material having Formula I and (b) one or more dopants. In some embodiments, the photoactive layer comprises (a) a host material having Formula I and (b) an organometallic electroluminescent dopant. In some embodiments, the photoactive layer comprises (a) a host material having Formula I, (b) a photoactive dopant, and (c) a second host material. In some embodiments, the photoactive layer comprises (a) a host material having Formula I, (b) an organometallic complex of Ir or Pt, and (c) a second host material. In some embodiments, the photoactive layer comprises (a) a host material having Formula I, (b) a cyclometallated complex of Ir, and (c) a second host material.

In some embodiments, the photoactive layer consists essentially of (a) a host material having Formula I and (b)

one or more dopants, where additional materials that would materially alter the principle of operation or the distinguishing characteristics of the layer are not present.

In some embodiments, the photoactive layer consists essentially of (a) a host material having Formula I and (b) an organometallic electroluminescent dopant, where additional materials that would materially alter the principle of operation or the distinguishing characteristics of the layer are not present. In some embodiments, the photoactive layer consists essentially of (a) a host material having Formula I, (b) a photoactive dopant, and (c) a second host material. In some embodiments, the photoactive layer consists essentially of (a) a host material having Formula I, (b) an organometallic complex of Ir or Pt, and (c) a second host material. In some embodiments, the photoactive layer consists essentially of (a) a host material having Formula I, (b) a cyclometallated complex of Ir, and (c) a second host material.

In some embodiments, the second host is selected from the group consisting of chrysenes, phenanthrenes, triphenylenes, phenanthrolines, triazines, naphthalenes, anthracenes, quinolines, isoquinolines, quinoxalines, phenylpyridines, carbazoles, indolocarbazoles, indoloindoles, furans, benzofurans, dibenzofurans, benzodifurans, metal quinolinate complexes, substituted derivatives thereof, and deuterated analogs thereof.

In some embodiments, the second host is selected from the group consisting of triphenylenes, carbazoles, indolocarbazoles, indoloindoles, furans, benzofurans, dibenzofurans, substituted derivatives thereof, and deuterated analogs thereof.

In some embodiments, the photoactive layer consists essentially of (a) a host material having Formula I, wherein the compound is deuterated, and (b) one or more dopants, where additional materials that would materially alter the principle of operation or the distinguishing characteristics of the layer are not present. In some embodiments, the photoactive layer consists essentially of a host material having Formula I, wherein the compound is deuterated, and (b) an organometallic electroluminescent dopant. In some embodiments, the photoactive layer consists essentially of (a) a host material having Formula I, wherein the compound is deuterated, (b) a photoactive dopant, and (c) a second host material. In some embodiments, the photoactive layer consists essentially of a host material having Formula I, wherein the compound is deuterated, (b) an organometallic complex of Ir or Pt, and (c) a second host material. In some embodiments, the photoactive layer consists essentially of (a) a host material having Formula I, wherein the compound is deuterated a host material having Formula I, wherein the compound is deuterated, (b) a cyclometallated complex of Ir, and (c) a second host material. In some embodiments, the deuterated compound of Formula I is at least 10% deuterated; in some embodiments, at least 50% deuterated. In some embodiments, the second host material is deuterated. In some embodiments, the second host material is at least 10% deuterated; in some embodiments, at least 50% deuterated.

In any of the above-described embodiments, the host compound can have Formula II.

In any of the above-described embodiments, the host compound can have Formula III.

In any of the above-described embodiments, the host compound can have Formula IV.

In any of the above-described embodiments, the host compound can have Formula V.

Electron Transport Layer

The compounds of Formula I are useful as electron transport materials in an electron transport layer. The compounds can be used alone, or in combination with another electron transport material.

In some embodiments, the electron transport layer comprises a compound having Formula I.

In some embodiments, the electron transport layer consists essentially of a compound having Formula I, where additional materials that would materially alter the principle of operation or the distinguishing characteristics of the layer are not present.

In any of the above-described embodiments, the electron transport material can have Formula II.

In any of the above-described embodiments, the electron transport material can have Formula III.

In any of the above-described embodiments, the electron transport material can have Formula IV.

In any of the above-described embodiments, electron transport material can have Formula V.

Examples of other electron transport materials which can be used alone or in combination with the compounds described herein include, but are not limited to, metal chelated oxinoid compounds, including metal quinolate derivatives such as tris(8-hydroxyquinolato)aluminum (AlQ), bis(2-methyl-8-quinolinolato)(p-phenylphenolato) aluminum (BAlq), tetrakis-(8-hydroxyquinolato)hafnium (HfQ) and tetrakis-(8-hydroxyquinolato)zirconium (ZrQ); and azole compounds such as 2-(4-biphenylyl)-5-(4-t-butylphenyl)-1,3,4-oxadiazole (PBD), 3-(4-biphenylyI)-4-phenyl-5-(4-t-butylphenyl)-1,2,4-triazole (TAZ), and 1,3,5-tri (phenyl-2-benzimidazole)benzene (TPBI); quinoxaline derivatives such as 2,3-bis(4-fluorophenyl)quinoxaline; phenanthrolines such as 4,7-diphenyl-1,10-phenanthroline (DPA) and 2,9-dimethyl-4,7-diphenyl-1,10-phenanthroline (DDPA); and mixtures thereof. In some embodiments, the electron transport material is selected from the group consisting of metal quinolates and phenanthroline derivatives. In some embodiments, the electron transport layer further comprises an n-dopant. N-dopant materials are well known. The n-dopants include, but are not limited to, Group 1 and 2 metals; Group 1 and 2 metal salts, such as LiF, CsF, and $Cs_2CO_3$; Group 1 and 2 metal organic compounds, such as Li quinolate; and molecular n-dopants, such as leuco dyes, metal complexes, such as $W_2(hpp)_4$ where hpp=1,3,4,6,7,8-hexahydro-2H-pyrimido-[1,2-a]-pyrimidine and cobaltocene, tetrathianaphthacene, bis(ethylenedithio)tetrathiafulvalene, heterocyclic radicals or diradicals, and the dimers, oligomers, polymers, dispiro compounds and polycycles of heterocyclic radical or diradicals.

Other Device Layers

The other layers in the device can be made of any materials that are known to be useful in such layers.

The anode is an electrode that is particularly efficient for injecting positive charge carriers. It can be made of, for example, materials containing a metal, mixed metal, alloy, metal oxide or mixed-metal oxide, or it can be a conducting polymer, or mixtures thereof. Suitable metals include the Group 11 metals, the metals in Groups 4-6, and the Group 8-10 transition metals. If the anode is to be light-transmitting, mixed-metal oxides of Groups 12, 13 and 14 metals, such as indium-tin-oxide, are generally used. The anode can also comprise an organic material such as polyaniline as described in "Flexible light-emitting diodes made from soluble conducting polymer," *Nature* vol. 357, pp 477-479

(11 Jun. 1992). At least one of the anode and cathode is desirably at least partially transparent to allow the generated light to be observed.

The hole injection layer comprises hole injection material and may have one or more functions in an organic electronic device, including but not limited to, planarization of the underlying layer, charge transport and/or charge injection properties, scavenging of impurities such as oxygen or metal ions, and other aspects to facilitate or to improve the performance of the organic electronic device. Hole injection materials may be polymers, oligomers, or small molecules. They may be vapour deposited or deposited from liquids which may be in the form of solutions, dispersions, suspensions, emulsions, colloidal mixtures, or other compositions.

The hole injection layer can be formed with polymeric materials, such as polyaniline (PANI) or polyethylenedioxythiophene (PEDOT), which are often doped with protonic acids. The protonic acids can be, for example, poly(styrenesulfonic acid), poly(2-acrylamido-2-methyl-1-propanesulfonic acid), and the like.

The hole injection layer can comprise charge transfer compounds, and the like, such as copper phthalocyanine and the tetrathiafulvalene-tetracyanoquinodimethane system (TTF-TCNQ).

In some embodiments, the hole injection layer comprises at least one electrically conductive polymer and at least one fluorinated acid polymer. In some embodiments, the hole injection layer comprises an electrically conductive polymer doped with a fluorinated acid polymer. materials have been described in, for example, published U.S. patent applications US 2004/0102577, US 2004/0127637, US 2005/0205860, and published PCT application WO 2009/018009.

Examples of hole transport materials for layer have been summarized for example, in Kirk-Othmer Encyclopedia of Chemical Technology, Fourth Edition, Vol. 18, p. 837-860, 1996, by Y. Wang. Both hole transporting molecules and polymers can be used. Commonly used hole transporting molecules are: N,N'-diphenyl-N,N'-bis(3-methylphenyl)-[1,1'-biphenyl]-4,4'-diamine (TPD), 1,1-bis[(di-4-tolylamino) phenyl]cyclohexane (TAPC), N, N'-bis(4-methylphenyl)-N,N'-bis(4-ethylphenyl)-[1,1'-(3,3'-dimethyl)biphenyl]-4,4'-diamine (ETPD), tetrakis-(3-methylphenyl)-N,N,N',N'-2,5-phenylenediamine (PDA), a-phenyl-4-N, N-diphenylaminostyrene (TPS), p-(diethylamino)benzaldehyde diphenylhydrazone (DEH), triphenylamine (TPA), bis[4-(N, N-diethylamino)-2-methylphenyl](4-methylphenyl)methane (MPMP), 1-phenyl-3[p-(diethylamino)styryl]-5-[p-(diethylamino)phenyl]pyrazoline (PPR or DEASP), 1,2-trans-bis(9H-carbazol-9-yl)cyclobutane (DCZB), N,N,N',N'-tetrakis(4-methylphenyl)-(1,1'-biphenyl)-4,4'-diamine (TTB), N,N'-bis(naphthalen-1-yl)-N,N'-bis-(phenyl)benzidine (α-NPB), and porphyrinic compounds, such as copper phthalocyanine. Commonly used hole transporting polymers are polyvinylcarbazole, (phenylmethyl)-polysilane, and polyaniline. It is also possible to obtain hole transporting polymers by doping hole transporting molecules such as those mentioned above into polymers such as polystyrene and polycarbonate. In some cases, triarylamine polymers are used, especially triarylamine-fluorene copolymers. In some cases, the polymers and copolymers are crosslinkable. In some embodiments, the hole transport layer further comprises a p-dopant. In some embodiments, the hole transport layer is doped with a p-dopant. Examples of p-dopants include, but are not limited to, tetrafluorotetracyanoquinodimethane (F4-TCNQ) and perylene-3,4,9,10-tetracarboxylic-3,4,9,10-dianhydride (PTCDA).

The cathode is an electrode that is particularly efficient for injecting electrons or negative charge carriers. The cathode can be any metal or nonmetal having a lower work function than the anode. Materials for the cathode can be selected from alkali metals of Group 1 (e.g., Li, Cs), the Group 2 (alkaline earth) metals, the Group 12 metals, including the rare earth elements and lanthanides, and the actinides. Materials such as aluminum, indium, calcium, barium, samarium and magnesium, as well as combinations, can be used. Li- or Cs-containing organometallic compounds, LiF, CsF, and $Li_2O$ can also be deposited between the organic layer and the cathode layer to lower the operating voltage.

It is known to have other layers in organic electronic devices. For example, there can be a layer (not shown) between the anode and hole injection layer to control the amount of positive charge injected and/or to provide bandgap matching of the layers, or to function as a protective layer. Layers that are known in the art can be used, such as copper phthalocyanine, silicon oxy-nitride, fluorocarbons, silanes, or an ultra-thin layer of a metal, such as Pt. Alternatively, some or all of anode layer, electroactive layers, or cathode layer, can be surface-treated to increase charge carrier transport efficiency. The choice of materials for each of the component layers is preferably determined by balancing the positive and negative charges in the emitter layer to provide a device with high electroluminescence efficiency.

It is understood that each functional layer can be made up of more than one layer.

The device can be prepared by a variety of techniques, including sequential vapor deposition of the individual layers on a suitable substrate. Substrates such as glass, plastics, and metals can be used. Conventional vapor deposition techniques can be used, such as thermal evaporation, chemical vapor deposition, and the like. Alternatively, the organic layers can be applied from solutions or dispersions in suitable solvents, using conventional coating or printing techniques, including but not limited to spin-coating, dip-coating, roll-to-roll techniques, ink-jet printing, screen-printing, gravure printing and the like.

In some embodiments, the device is fabricated by liquid deposition of the buffer layer, the hole transport layer, and the photoactive layer, and by vapor deposition of the anode, the electron transport layer, an electron injection layer and the cathode.

To achieve a high efficiency LED, the HOMO (highest occupied molecular orbital) of the hole transport material desirably aligns with the work function of the anode, and the LUMO (lowest un-occupied molecular orbital) of the electron transport material desirably aligns with the work function of the cathode. Chemical compatibility and sublimation temperature of the materials may also be considerations in selecting the electron and hole transport materials.

It is understood that the efficiency of devices made with the compounds described herein, can be further improved by optimizing the other layers in the device. For example, more efficient cathodes such as Ca, Ba or LiF can be used. Shaped substrates and novel hole transport materials that result in a reduction in operating voltage or increase quantum efficiency are also applicable. Additional layers can also be added to tailor the energy levels of the various layers and facilitate electroluminescence.

EXAMPLES

The concepts described herein will be further described in the following examples, which do not limit the scope of the invention described in the claims.

Synthesis Example 1

This example illustrates the synthesis of a compound having Formula II, Compound A1.

A1A

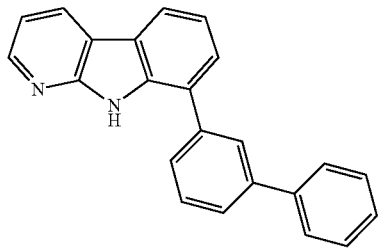

(a) Synthesis of Intermediate Compound A1A 2.0 g of 1-aza-8-chlorocarbazole (10 mMoles) was placed in a dried flask in a nitrogen filled glove box and 2.2 g (11 mMoles) 3-biphenyl boronic acid was added. 0.24 g Pd2DBA3 (0.24 mMoles), 0.14 g tricyclohexylphosphine (0.48 mMmoles) and 3.4 g tribasic potassium phosphate (11 mMoles) and were added as dry solids and then the whole mixture was dissolved into 50 mL dioxane and 25 mL degassed water. The resulting slurry was stirred and heated in the glove box at 100 C for 2 hr and then warmed gently (just below reflux) for another hour. The solution is immediately red brown and cloudy but on reaching ~100 C it becomes a dark clear red brown. TLC (silica plates) shows a new spot running just ahead of the starting carbazole using DCM or THF/toluene as eluents. The reaction was cooled and removed from the glove box and 50 mL water was added. The mixture was extracted into DCM and the organic layer was collected and dried over magnesium sulfate. The resulting red brown solution was chromatographed through a stacked bed of silica/basic-alumina/florisil eluting with DCM to collect a pale yellow solution which was evaporated down to generate a pale yellow solid. Recrystallization from DCM/acetonitrile yielded an off-white solid whose 1-H nmr spectrum confirmed the anticipated structure MA. Yield 2.25 g (b) Synthesis of Intermediate Compound A1B

A1B

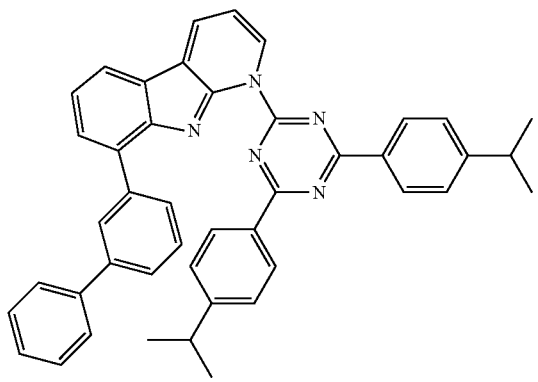

2.5 g of intermediate A1A from above was slurried into 75 mL dry THF in a nitrogen filled glove box and 0.222 g sodium hydride was added with stirring. After 30 mins, 2.75 g 1,3,5-Triazine, 2-chloro-4,6-bis[4-(1-methylethyl)phenyl]- was added as a solid over a period of 10 mins. The slurry rapidly darkens to a deep red after heating to 40 C. The red slurry was filtered through a fine frit and the filter cake was washed with dry THF until all red color was eluted. Evaporation of the red solution yielded golden yellow solid of structure A1B as confirmed by 1-H nmr and single crystal analysis. Yield ~75%.

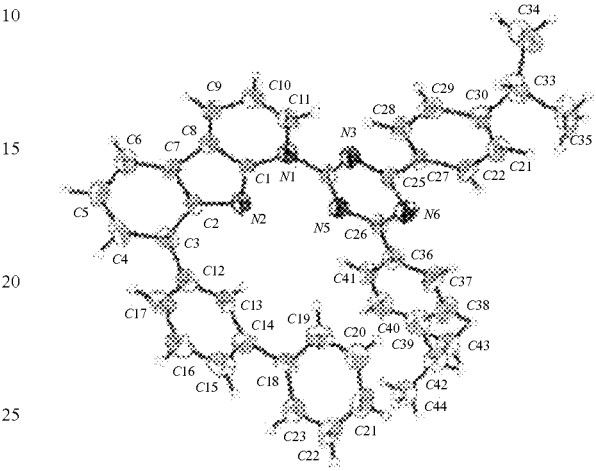

Treatment of a THF or methylene chloride solution of compound A1B with methanol or water rapidly decolorized the deep red solution to a pale yellow and 1-H nmr indicates reversal of the coupled product to starting material MA and triazine containing materials.

(c) Synthesis of Compound A1.

0.46 g of golden yellow solid A1B from above was heated in a nitrogen filled glove box at 260 C for 140 minutes in a heating block. The recovered solid was cooled and extracted into toluene and chromatographed through silica eluting with toluene to collect 0.43 g of white solid after evaporation of extracts. The white solid was recrystallized from methylene chloride/heptane to yield diffraction quality single crystals. The structure of A1 was confirmed by 1-H nmr and single crystal X-ray diffraction

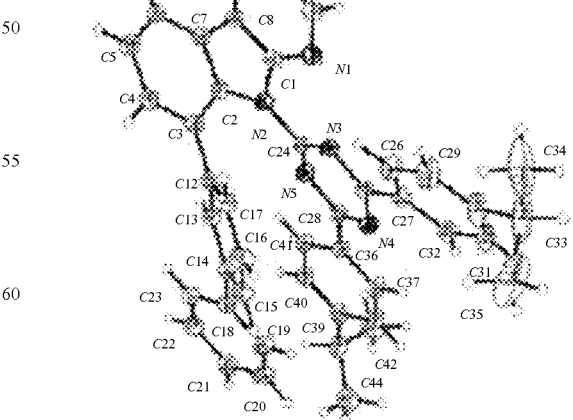

Synthesis Example 2

This example illustrates the synthesis of a compound having Formula II, Compound A2.

(a) Synthesis of Intermediate Compound A2B

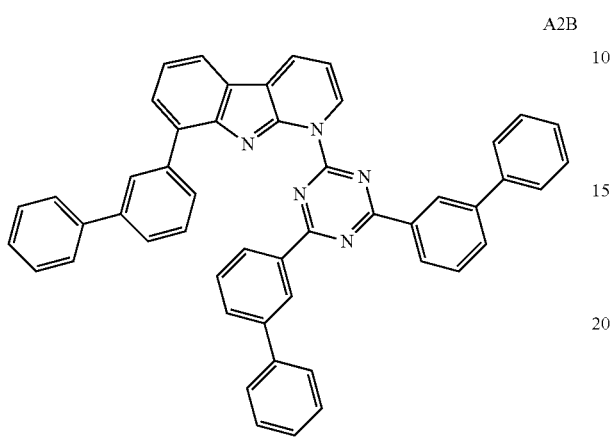

A2B 3.5 g of intermediate A1A from above was slurried into 125 mL dry THF in a nitrogen filled glove box and 0.32 g sodium hydride was added with stirring. After 4 hrs, 4.725 g 1,3,5-Triazine, 2,4-bis([1,1'-biphenyl]-3-yl)-6-chloro- was added as a solid over a period of 10 mins. The slurry rapidly darkens to a deep red after heating to 40 C. The red slurry was filtered through a fine frit and the filter cake was washed with dry THF until all red color was eluted. Evaporation of the red solution yielded golden yellow crude solid of structure A2B (b) Synthesis of Compound A2.

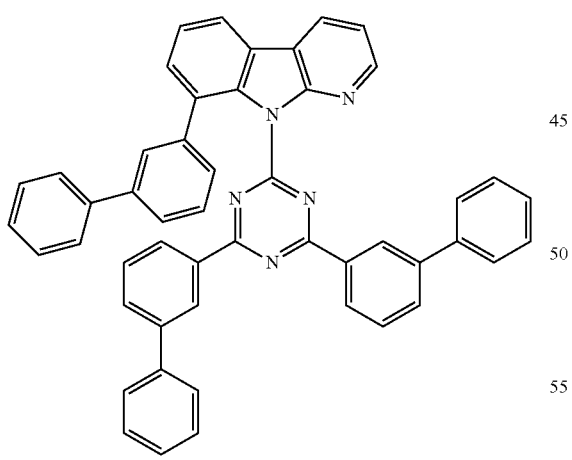

A2

The crude golden yellow solid A2B from above was heated in a nitrogen filled glove box at 265 C for 150 minutes in a heating block. The recovered solid was cooled and chromatographed through silica eluting with dichloromethane/hexanes to collect a white solid after evaporation of extracts. The white solid was recrystallized from acetonitrile/toluene to yield 3.0 g white crystals. Structure A2 is confirmed by nmr spectroscopy.

Synthesis Example 3

This example illustrates the synthesis of a compound having Formula II, Compound A3.

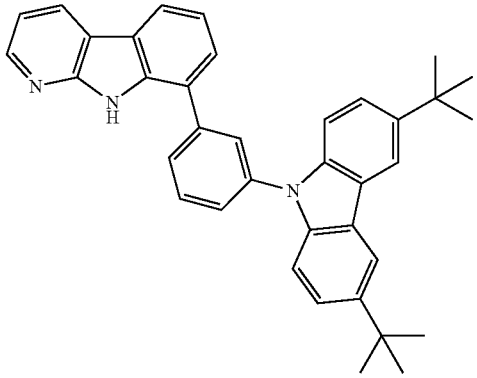

A3A (a) Synthesis of Intermediate Compound A3A

Following the same procedure as described above for intermediate A1A but substituting 3,6-di-t-butyl-9-(3-phenylboronate)-carbazole for the biphenylboronic acid yielded intermediate A3A.

(b) Synthesis of Intermediate Compound A3B

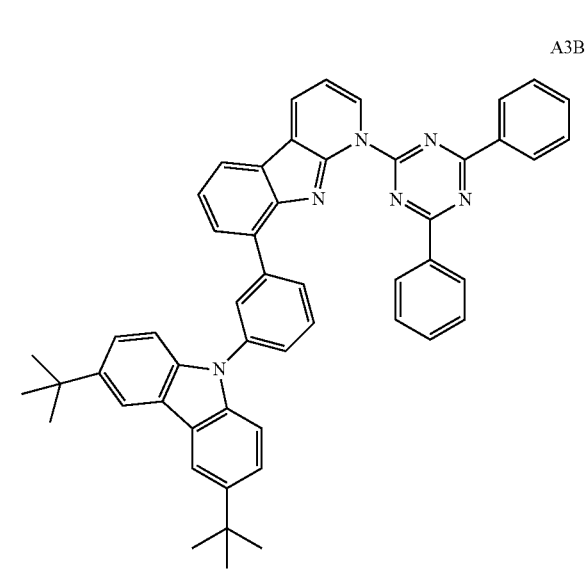 [SMILES: CC(C)(C)c1ccc2c(c1)c1cc(C(C)(C)C)ccc1n2-c1cccc(-c2cccc3c4cccn(-c5nc(-c6ccccc6)nc(-c6ccccc6)n5)c-4nc23)c1]

A3B 1.37 g of intermediate A3A from above was slurried into 35 mL dry THF in a nitrogen filled glove box and 0.075 g sodium hydride was added with stirring. After 30 mins, 2.75 g 1,3,5-Triazine, 2-chloro-4,6-bis[phenyl]- was added as a solid over a period of 90 mins. The slurry rapidly darkens to a deep red after heating to 50 C. The red slurry was filtered through a fine frit and the filter cake was washed with dry THF until all red color was eluted. Evaporation of the red solution yielded a crude golden yellow solid of structure A3B.

(c) Synthesis of Compound A3.

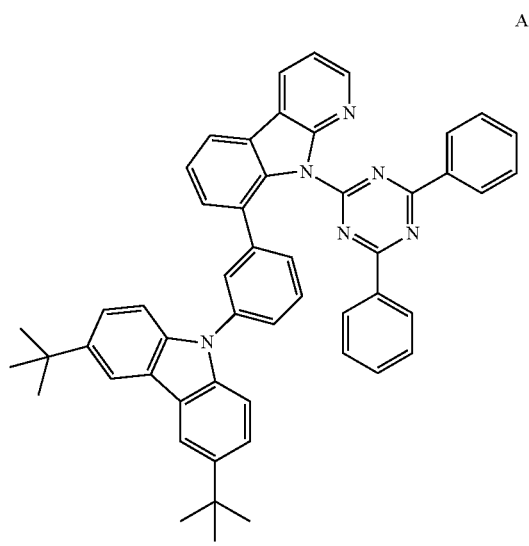

The crude golden yellow solid A3B from above was heated in a nitrogen filled glove box at 260 C for 155 minutes in a heating block. The recovered solid was cooled and extracted into chloroform and chromatographed through silica eluting with chloroform/hexanes to collect ~0.45 g of white solid after evaporation of extracts. The white solid was recrystallized from methylene chloride/hexanes to yield 0.4 g white crystals. The structure of A3 was confirmed by 1-H nmr spectroscopy.

Synthesis Example 4

This example illustrates the synthesis of a compound having Formula II, Compound A4.

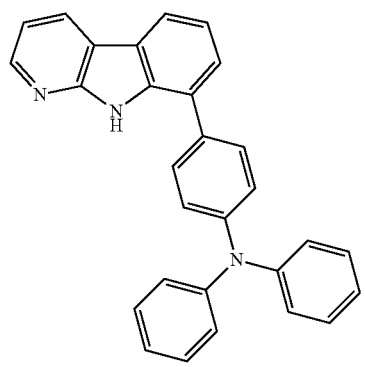

(a) Synthesis of Intermediate Compound A4A

Following the same procedure as described above for intermediate A1A but substituting 4-diphenylamino-phenyl-boronic acid for the biphenylboronic acid yielded intermediate A4A.

(b) Synthesis of Intermediate Compound A4B

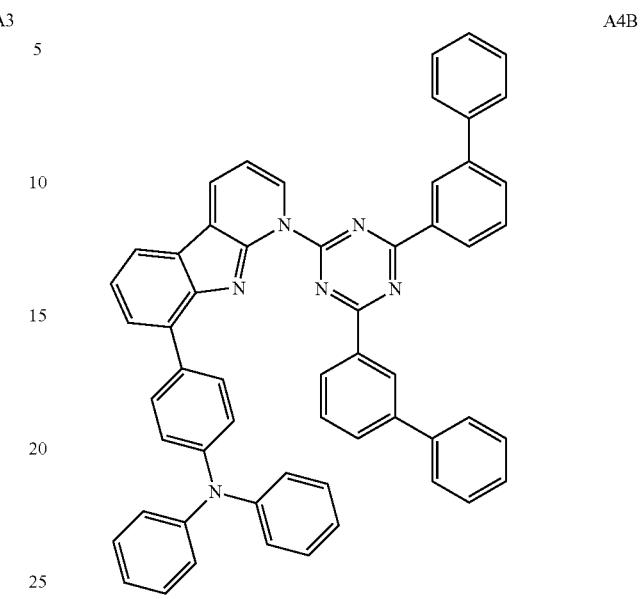

3.4 g of intermediate A4A from above was slurried into 120 mL dry THF in a nitrogen filled glove box and 0.238 g sodium hydride was added with stirring. After 150 mins, 3.57 g 1,3,5-Triazine, 2,4-bis([1,1'-biphenyl]-3-yl)-6-chloro- was added. The slurry rapidly darkens to a deep red after heating to 50 C. The red slurry was filtered through a fine frit and the filter cake was washed with dry THF until all red color was eluted. Evaporation of the red solution yielded a crude golden yellow solid of structure A4B (c) Synthesis of Compound A4.

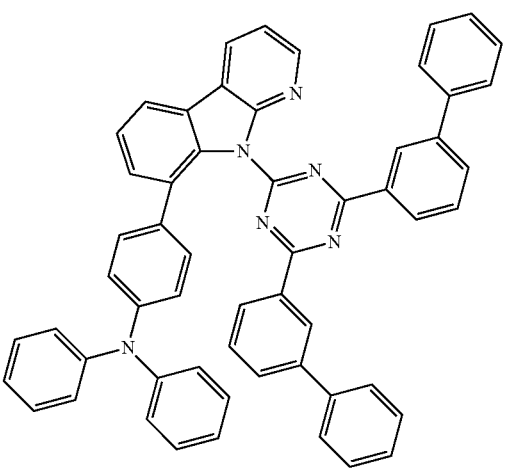

The crude golden yellow solid A4B from above was heated in a nitrogen filled glove box at 260 C for 155 minutes in a heating block. The recovered solid was cooled and extracted into dichloromethane and chromatographed through alumina eluting with dichloromethane and through silica eluting with dichloromethane/hexanes to collect a white solid after evaporation of extracts. The white solid was recrystallized from toluene/acetonitrile to yield 2.5 g white crystals. The structure of A4 was confirmed by 1-H nmr spectroscopy.

Synthesis Example 5

This example illustrates the synthesis of a compound having Formula II, Compound A5.

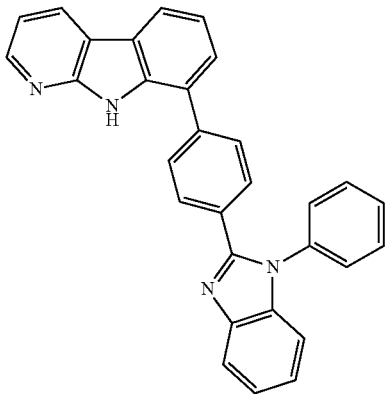

A5A (a) Synthesis of Intermediate Compound A5A

Following the same procedure as described above for intermediate A1A but substituting 1-phenyl,2-(4-phenylboronate)benzimidazole for the biphenylboronic acid yielded intermediate A5A.

(b) Synthesis of Intermediate Compound A5B

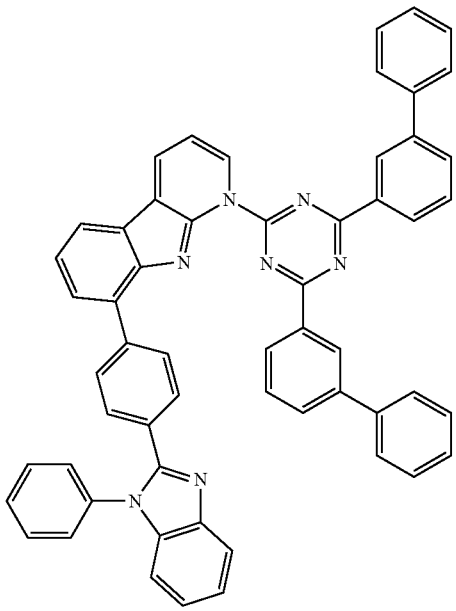

A5B 4.3 g of intermediate A5A from above was slurried into 150 mL dry THF in a nitrogen filled glove box and 0.284 g sodium hydride was added with stirring. After 30 mins, 4.21 g 1,3,5-Triazine, 2,4-bis([1,1'-biphenyl]-3-yl)-6-chloro was added as a solid over a period of 90 mins. The slurry rapidly darkens to a deep red after heating to 50 C. The red slurry was filtered through a fine frit and the filter cake was washed with dry THF until all red color was eluted. Evaporation of the red solution yielded a crude golden yellow solid of structure A5B (c) Synthesis of Compound A5.

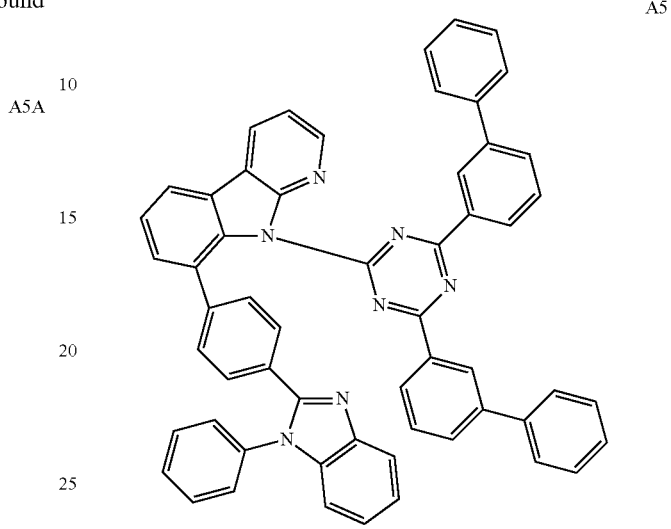

A5

The crude golden yellow solid A5B from above was heated in a nitrogen filled glove box at 260 C for 150 minutes in a heating block. The recovered solid was cooled and extracted into dichloromethane and chromatographed through alumina eluting with dichloromethane and then recrystallized from toluene/acetonitrile to yield 4.7 g white crystals. The structure of A5 was confirmed by 1-H nmr spectroscopy.

Synthesis Example 6

This example illustrates the synthesis of a compound having Formula II, Compound A6.

(b) Synthesis of Intermediate Compound A6B

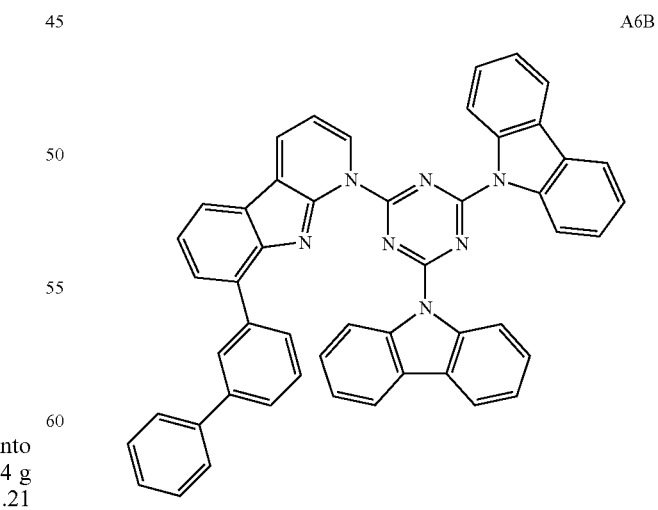

A6B 3.0 g of intermediate A1A from above was slurried into 105 mL dry THF in a nitrogen filled glove box and 0.27 g sodium hydride was added with stirring. After 30 mins, 4.45 g 9H-Carbazole, 9,9'-(6-chloro-1,3,5-triazine-2,4-diyl)bis- was added as a solid over a period of 90 mins. The slurry rapidly darkens to a deep red after heating to 50 C. The red slurry was held at 50 C overnight and then filtered through a fine frit and the filter cake was washed with dry THF until all red color was eluted. Evaporation of the red solution yielded a crude red yellow solid of structure A6B (c) Synthesis of Compound A6.

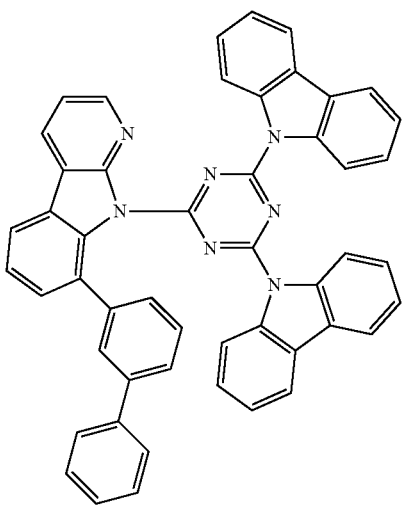

A6

The crude golden yellow solid A6B from above was heated in a nitrogen filled glove box at 295 C for 120 minutes in a heating block. The recovered solid was cooled and extracted into toluene and chromatographed through silica eluting with chloroform/hexanes and then recrystallized from toluene/heptane to yield 3.5 g crystals. The structure of A6 was confirmed by 1-H nmr spectroscopy.

Synthesis Example 7

This example illustrates the synthesis of a compound having Formula II, Compound A7.

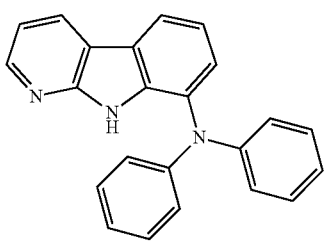

A7A (a) Synthesis of Intermediate Compound A7A

In a nitrogen filled drybox a round bottom flask was charged with Pd$_2$DBA$_3$ (4.80 g), 2-dicyclohexylphosphino-2',4',6'-triisopropylbiphenyl (5.0 g), lithium bis(trimethylsilyl)amide (32.18 g), 1-aza-8-chlorocarbazole (15.90 g) and 470 ml of o-xylene with stirring for ten minutes followed by addition of diphenylamine (15.7 g). The mixture was heated to 140° C. overnight and then concentrated to perform a separation by a DCM/chloroform/toluene/water partition. The organic layer was filtered through a silica plug and preabsorbed from DCM to 66 g of silica gel.

Column chromatography on silica eluting with DCM/hexanes yielded 10.5 g of product A7A. as an off-white solid confirmed by 1-H nmr.

(b) Synthesis of Intermediate Compound A7B

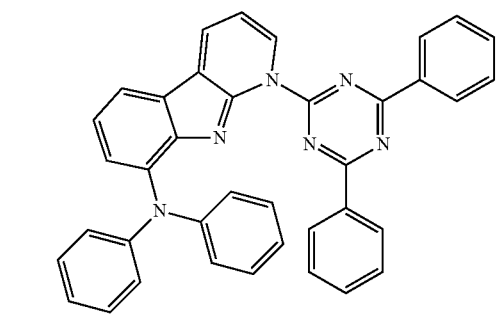

A7B 9.2 g of intermediate A7A from above was slurried into 320 mL dry THF in a nitrogen filled glove box and 0.81 g sodium hydride was added with stirring. After 30 mins, 7.54 g 1,3,5-Triazine, 2,4-diphenyl-6-chloro- was added as a solid over a period of 90 mins. The slurry rapidly darkens to a deep red after heating to 50 C. The red slurry was held at 50 C overnight and was then evaporated to a crude golden yellow solid of structure A7B (c) Synthesis of Compound A7.

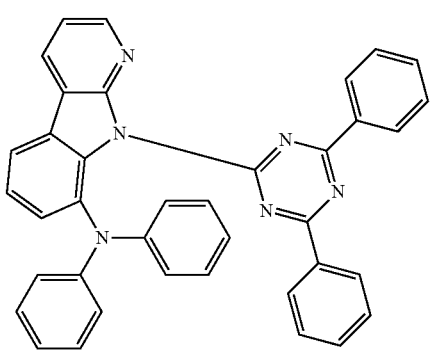

A7

The crude golden yellow solid A7B from above was heated in a nitrogen filled glove box at 250 C for 225 minutes in a heating block. The recovered solid was cooled and extracted into dichloromethane and chromatographed through silica eluting with dichloromethane/hexanes and then recrystallized from toluene/acetonitrile to yield 12 g white crystals. The structure of A7 was confirmed by 1-H nmr spectroscopy.

Example 1

The triplet energies were calculated for Compounds A1 through A7. The calculations were performed with the density functional theory (DFT) methods within the Gaussian 03 suite of programs. (Gaussian 03, revision D.01; Gaussian, Inc., Wallingford, C T, 2004). The molecular structures were first optimized at the BP86/6-31 G+IrMWB60 level and then used in subsequent analytic vibrational frequency calculations at this same level of computation to ensure that these structures were indeed equilibrium ones. For the excited-state calculations, previous experience has shown that time-dependent DFT (TDDFT) at the B3LYP/6-31G+IrMWB60 level is satisfactory in computing the first seven singlet and triplet energy transitions. In order to obtain HOMO and LUMO values for these molecules, the B3LYP/6-31+G(d)+IrMWB60 level was used. The results are given in Table 1.

TABLE 1

| Triplet Energies | |
|---|---|
| Compound | Calculated triplet energy |
| A1 | 2.89 eV |
| A2 | 2.87 eV |
| A3 | 2.67 eV |
| A4 | 2.32 eV |
| A5 | 2.67 eV |
| A6 | 2.96 eV |
| A7 | 2.43 eV |

Device Examples (1) Materials

Dopant D1, shown below, is a cyclometallated iridium complex. Such materials have been described in, for example, published PCT application WO 2013142634.

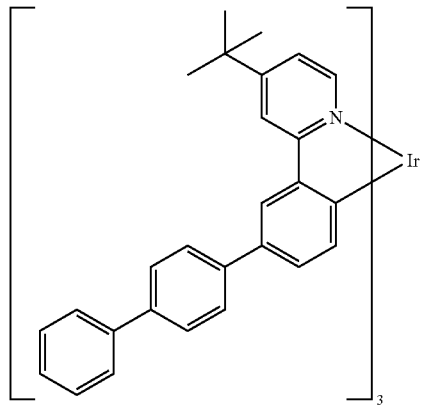

ET-1 is an aryl phosphine oxide.

ET-2 is lithium quinolate.

HIJ-1 is a hole injection material which is made from an aqueous dispersion of an electrically conductive polymer and a polymeric fluorinated sulfonic acid. Such materials have been described in, for example, U.S. Pat. No. 7,351,358 and published PCT application WO 2009/018009.

Host H2, shown below, is an indolocarbazole. Such materials have been described in, for example, published PCT Application WO 2012087955.

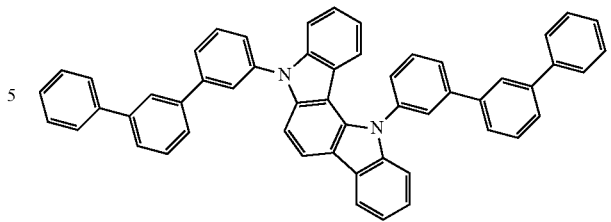

HTM-1 is a triarylamine polymer. Such materials have been described in, for example, published PCT Application WO 2011159872.

HTM-2 is an aromatic compound having multiple phenyl groups. Such materials have been described in, for example, published PCT Application WO 2015089304.

(2) Device Fabrication

OLED devices were fabricated by a combination of solution processing and thermal evaporation techniques. Patterned indium tin oxide (ITO) coated glass substrates from Thin Film Devices, Inc were used. These ITO substrates are based on Corning 1737 glass coated with ITO having a sheet resistance of 30 ohms/square and 80% light transmission. The patterned ITO substrates were cleaned ultrasonically in aqueous detergent solution and rinsed with distilled water. The patterned ITO was subsequently cleaned ultrasonically in acetone, rinsed with isopropanol, and dried in a stream of nitrogen.

Immediately before device fabrication the cleaned, patterned ITO substrates were treated with UV ozone for 10 minutes. Immediately after cooling, an aqueous dispersion of HIJ-1 was spin-coated over the ITO surface and heated to remove solvent. After cooling, the substrates were then spin-coated with a toluene solution of hole transport material, and then heated to remove solvent. After cooling the substrates were spin-coated with a methyl benzoate solution of the host and dopant, and heated to remove solvent. The substrates were masked and placed in a vacuum chamber. A layer of electron transport material was deposited by thermal evaporation, followed by a layer of electron injection material. Masks were then changed in vacuum and a layer of Al was deposited by thermal evaporation. The chamber was vented, and the devices were encapsulated using a glass lid, dessicant, and UV curable epoxy.

(3) Device Characterization

The OLED devices were characterized by measuring their (1) current-voltage (I-V) curves, (2) electroluminescence radiance versus voltage, and (3) electroluminescence spectra versus voltage. All three measurements were performed at the same time and controlled by a computer. The current efficiency of the device at a certain voltage is determined by dividing the electroluminescence radiance of the LED by the current density needed to run the device. The unit is a cd/A. The power efficiency is the current efficiency divided by the operating voltage. The unit is lm/W. The color coordinates were determined using either a Minolta CS-100 meter or a Photoresearch PR-705 meter.

Device Example 1-3

These examples illustrate the use of a material having Formula I, Compound A7, as the host material in a device. The devices had the following layers.

Anode=ITO (50 nm)
HIL=HIJ-1 (50 nm)
HTL=HTM-2:HTM-3 (8:2) (18 nm)
EML=Host H2:Compound A7: Dopant D1 in the weight ratios given in Table 2 (53 nm)
ETL=ET-1:ET-2 (2:3) (20 nm)
Cathode=Al (100 nm)
The results are given in Table 2 below.

TABLE 2

Device results

| Ex. | Ratio (H2:A7:D1) | CE (cd/A) | EQE (%) | T95 (hours) |
|---|---|---|---|---|
| 1 | 40:44:16 | 57 | 16 | 36 |
| 2 | 30:54:16 | 68 | 19 | 27 |
| 3 | 50:34:16 | 53 | 14 | 42 |

Ratio is the weight ratio. All data, except T95, are at 2000 nits. CE is the current efficiency; EQE = external quantum efficiency; T95 is the time in hours for a device to reach 95% of the initial luminance at 5 mA/cm2 and 50° C.

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

It is to be appreciated that certain features are, for clarity, described herein in the context of separate embodiments, may also be provided in combination in a single embodiment. Conversely, various features that are, for brevity, described in the context of a single embodiment, may also be provided separately or in any subcombination. Further, reference to values stated in ranges include each and every value within that range.

What is claimed is:

1. A compound having Formula II $$(R^1)_a \text{—[carbazole core]—} (R^2)_{a1}, \text{Ar}^1, \text{Ar}^2 \quad (II)$$

wherein:
Ar$^1$ is selected from the group consisting of an N-heterocycle and a substituted N-heterocycle, wherein substituents of the substituted N-heterocycle are selected from the group consisting of D, alkyl, silyl, germyl, hydrocarbon aryl, alkylaryl, silylaryl, heteroaryl, deuterated analogs thereof, and combinations thereof;

Ar$^2$ selected from the group consisting of diarylamino,

[benzimidazole structure with Y substituent]

substituted derivatives thereof, and deuterated analogs thereof, where Y is an aryl group and attached to N-carbazolyl of Formula II;

R$^1$ and R$^2$ are the same or different at each occurrence and are selected from the group consisting of D, alkyl, silyl, germyl, hydrocarbon aryl, heteroaryl, and deuterated analogs thereof; and a and a1 are the same or different and are integers from 0-3.

2. The compound of claim 1, wherein the N-heterocycle and substituted N-heterocycle are selected from the group consisting of pyridine, pyrimidine, triazine, and a deuterated analog thereof.

3. The compound of claim 1, wherein Ar$^2$ is substituted with at least one substituent selected from the group consisting of silyl, aryl, alkylaryl, silylaryl, N-heteroaryl, deuterated analogs thereof, and combinations thereof.

4. The compound of claim 1, wherein Ar$^2$ is a diarylamino group or deuterated analog thereof.

5. The compound of claim 1, wherein a=a1=0.

6. An electronic device having at least one layer comprising the compound of Formula II according to claim 1.

7. The electronic device of claim 6, wherein the layer comprising the compound of Formula II is a photoactive layer.

8. The electronic device of claim 7, wherein the layer further comprises an electroluminescent dopant.

9. The electronic device of claim 6, wherein the layer comprising the compound of Formula II is an electron transport layer.

10. A compound selected from the following:

Compound A5

[chemical structure]

Compound A7
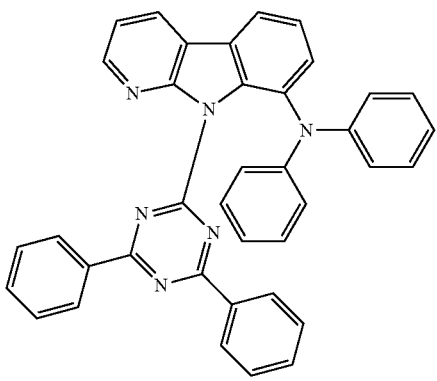
Compound A11
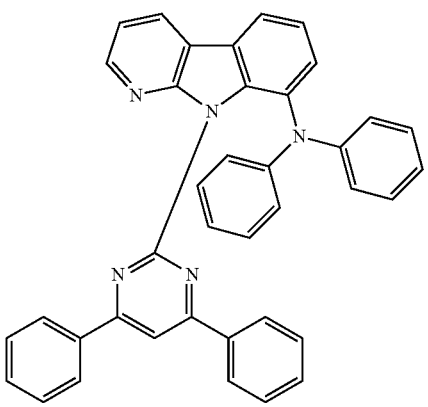
Compound A12
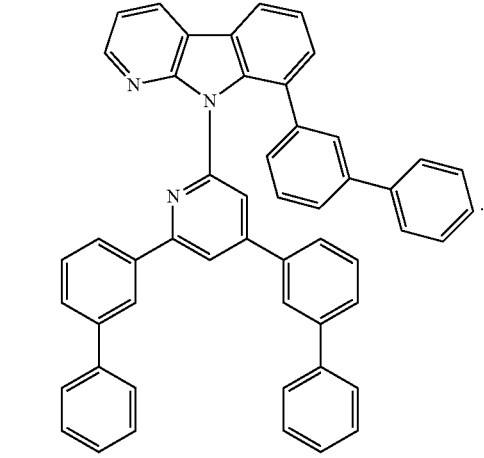
11. The compound of claim 1, wherein the N-heterocycle of Ar¹ is selected from the group consisting of
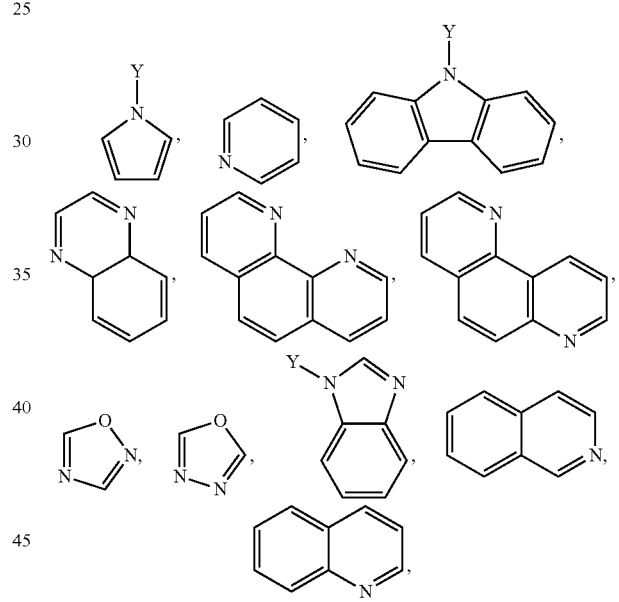
and deuterated analogs thereof, wherein Y is an aryl group.
* * * * *